(12) United States Patent
Kassab

(10) Patent No.: US 11,103,152 B2
(45) Date of Patent: Aug. 31, 2021

(54) IMPEDANCE DEVICES AND METHODS OF USING THE SAME TO OBTAIN LUMINAL ORGAN MEASUREMENTS

(71) Applicant: 3DT Holdings, LLC, San Diego, CA (US)

(72) Inventor: Ghassan S. Kassab, La Jolla, CA (US)

(73) Assignee: 3DT Holdings, LLC, San Diego, CA (US)

(*) Notice: Subject to any disclaimer, the term of this patent is extended or adjusted under 35 U.S.C. 154(b) by 130 days.

(21) Appl. No.: 15/290,919

(22) Filed: Oct. 11, 2016

(65) Prior Publication Data

US 2017/0027475 A1 Feb. 2, 2017

Related U.S. Application Data

(60) Continuation-in-part of application No. 14/755,096, filed on Jun. 30, 2015, now abandoned, and a
(Continued)

(51) Int. Cl.
| | |
|---|---|
| *A61B 5/0538* | (2021.01) |
| *A61B 5/107* | (2006.01) |
| *A61B 5/00* | (2006.01) |
| *A61B 5/0215* | (2006.01) |
| *A61B 5/01* | (2006.01) |

(Continued)

(52) U.S. Cl.
CPC ............ *A61B 5/0538* (2013.01); *A61B 5/01* (2013.01); *A61B 5/02158* (2013.01); *A61B 5/036* (2013.01); *A61B 5/1076* (2013.01); *A61B 5/6853* (2013.01); *A61B 18/1492* (2013.01); *A61B 2017/00026* (2013.01); *A61B 2018/00577* (2013.01); *A61B 2018/00648* (2013.01); *A61B 2018/00791* (2013.01);
(Continued)

(58) Field of Classification Search
CPC ... A61B 18/1492; A61B 5/01; A61B 5/02158; A61B 5/036; A61B 5/0538; A61B 5/1076; A61B 5/6853
See application file for complete search history.

(56) References Cited

U.S. PATENT DOCUMENTS

| | | | | | |
|---|---|---|---|---|---|
| 4,387,723 | A | * | 6/1983 | Atlee, III | A61B 5/1106 600/547 |
| 5,851,191 | A | * | 12/1998 | Gozani | A61B 5/1106 600/554 |

(Continued)

FOREIGN PATENT DOCUMENTS

JP 05123304 A * 5/1993 ......... A61B 18/1492

*Primary Examiner* — Sean P Dougherty
(74) *Attorney, Agent, or Firm* — Reichel Stohry Dean LLP; Mark C. Reichel; Natalie J. Dean

(57) ABSTRACT

Impedance devices and methods of using the same to obtain luminal organ measurements. In at least one embodiment of an impedance device of the present disclosure, the impedance device comprises an elongated body having a distal body end, and a first electrode located along the elongated body at or near the distal body end, the first electrode configured to obtain one or more conductance values within a mammalian luminal organ within an electric field, wherein a measured parameter of the mammalian luminal organ can be calculated based in part upon the one or more conductance values obtained by the first electrode.

16 Claims, 14 Drawing Sheets

Related U.S. Application Data continuation-in-part of application No. 14/580,580, filed on Dec. 23, 2014, now abandoned, and a continuation of application No. 14/215,012, filed on Mar. 16, 2014, now Pat. No. 9,462,960, said application No. 14/580,580 is a continuation of application No. 13/372,573, filed on Feb. 14, 2012, now Pat. No. 8,918,169, said application No. 14/755,096 is a continuation of application No. 13/324,222, filed on Dec. 13, 2011, now Pat. No. 9,066,708, which is a continuation of application No. 12/098,242, filed on Apr. 4, 2008, now Pat. No. 8,078,274, said application No. 13/372,573 is a continuation of application No. 11/891,981, filed on Aug. 14, 2007, now Pat. No. 8,114,143, said application No. 12/098,242 is a continuation-in-part of application No. 11/891,981, which is a division of application No. 10/782,149, filed on Feb. 19, 2004, now Pat. No. 7,454,244.

(60) Provisional application No. 61/800,407, filed on Mar. 15, 2013, provisional application No. 60/502,139, filed on Sep. 11, 2003, provisional application No. 60/493,145, filed on Aug. 7, 2003, provisional application No. 60/449,266, filed on Feb. 21, 2003.

(51) Int. Cl.
  *A61B 5/03* (2006.01)
  *A61B 18/14* (2006.01)
  *A61B 17/00* (2006.01)
  *A61B 18/00* (2006.01)

(52) U.S. Cl.
  CPC ............... *A61B 2018/00875* (2013.01); *A61B 2218/001* (2013.01); *A61B 2562/0217* (2017.08)

(56) References Cited

U.S. PATENT DOCUMENTS

| | | | | |
|---|---|---|---|---|
| 6,466,811 B1* | 10/2002 | Hassett | | A61B 5/0422 600/374 |
| 6,892,091 B1* | 5/2005 | Ben-Haim | | A61B 5/0422 600/509 |
| 7,300,438 B2* | 11/2007 | Falwell | | A61B 18/1492 606/41 |
| 2002/0095098 A1* | 7/2002 | Marinello | | A61B 5/1106 600/544 |
| 2002/0143326 A1* | 10/2002 | Foley | | A61B 18/1492 606/41 |
| 2002/0161306 A1* | 10/2002 | Govari | | A61B 5/0422 600/509 |
| 2003/0125614 A1* | 7/2003 | Fuimaono | | A61B 5/0422 600/374 |
| 2004/0044277 A1* | 3/2004 | Fuimaono | | A61B 5/0422 600/374 |
| 2004/0186468 A1* | 9/2004 | Edwards | | A61B 18/1477 606/41 |
| 2004/0187875 A1* | 9/2004 | He | | A61B 18/1492 128/898 |
| 2004/0242984 A1* | 12/2004 | Plaza | | A61B 5/0422 600/374 |
| 2004/0243011 A1* | 12/2004 | Plaza | | A61B 5/0422 600/509 |
| 2005/0049542 A1* | 3/2005 | Sigg | | A61N 1/327 604/20 |
| 2005/0203434 A1* | 9/2005 | Kassab | | A61B 5/02007 600/547 |
| 2006/0276685 A1* | 12/2006 | Dinsmore | | A61K 35/28 600/37 |
| 2007/0225610 A1* | 9/2007 | Mickley | | A61B 5/0422 600/509 |
| 2007/0287933 A1* | 12/2007 | Phan | | A61B 10/0233 600/566 |
| 2008/0262337 A1* | 10/2008 | Falwell | | A61B 18/1492 600/374 |
| 2009/0099468 A1* | 4/2009 | Thiagalingam | | A61B 5/0452 600/515 |
| 2010/0081963 A1* | 4/2010 | Gilhuly | | A61B 5/746 600/554 |
| 2010/0198040 A1* | 8/2010 | Friedman | | A61B 5/0422 600/374 |
| 2010/0274150 A1* | 10/2010 | Harlev | | A61B 5/0422 600/523 |
| 2011/0264000 A1* | 10/2011 | Paul | | A61B 5/0537 600/547 |
| 2013/0204155 A1* | 8/2013 | Brull | | A61B 5/4821 600/546 |
| 2013/0204156 A1* | 8/2013 | Hampton | | A61B 5/4052 600/546 |
| 2014/0235991 A1* | 8/2014 | Gadsby | | A61B 5/24 600/391 |
| 2018/0333569 A1* | 11/2018 | Snow | | A61B 5/4821 |
| 2019/0223764 A1* | 7/2019 | Hulvershorn | | A61B 5/1106 |

* cited by examiner

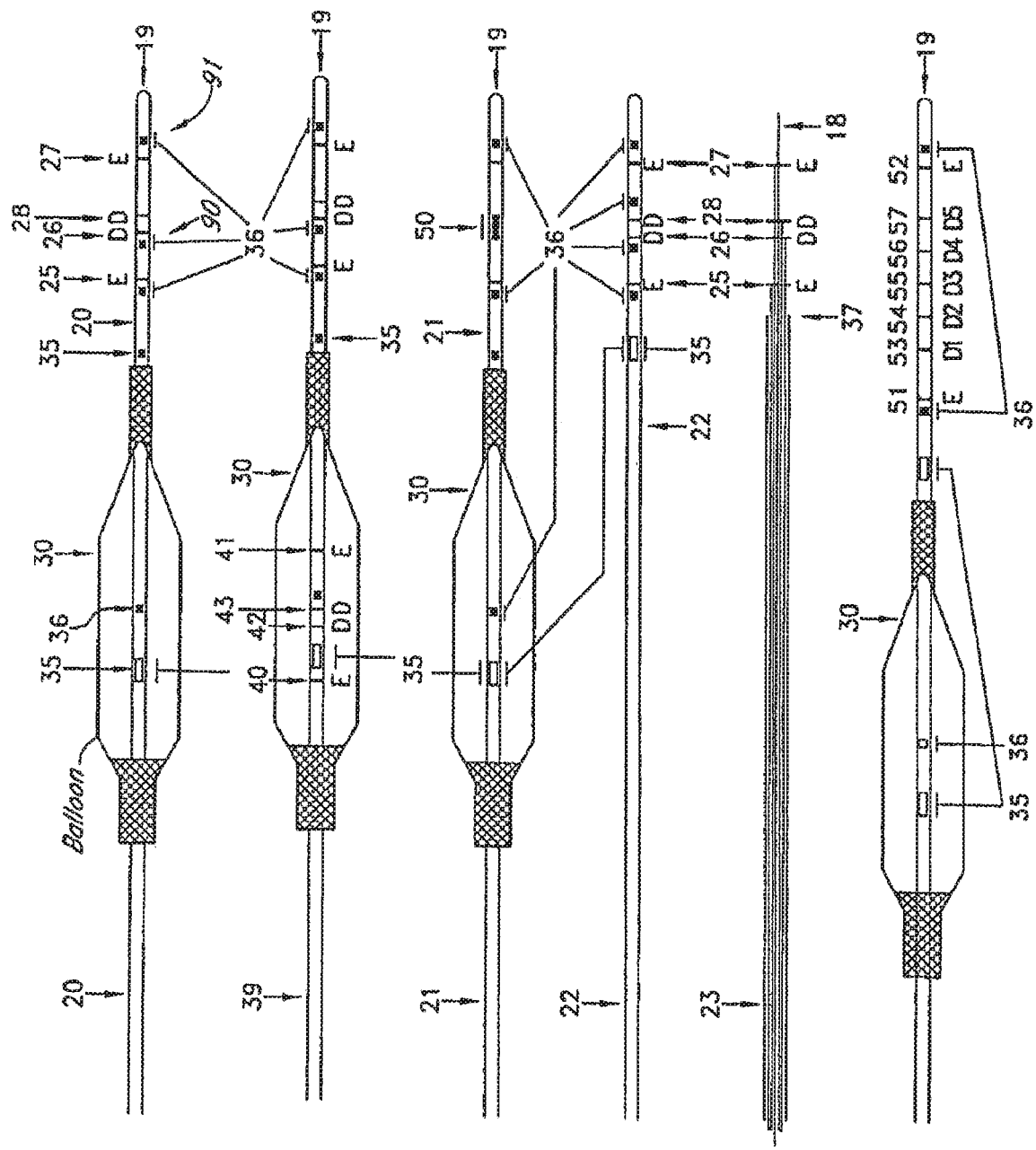

envelope data peak-peak of voltage at the detection electrodes

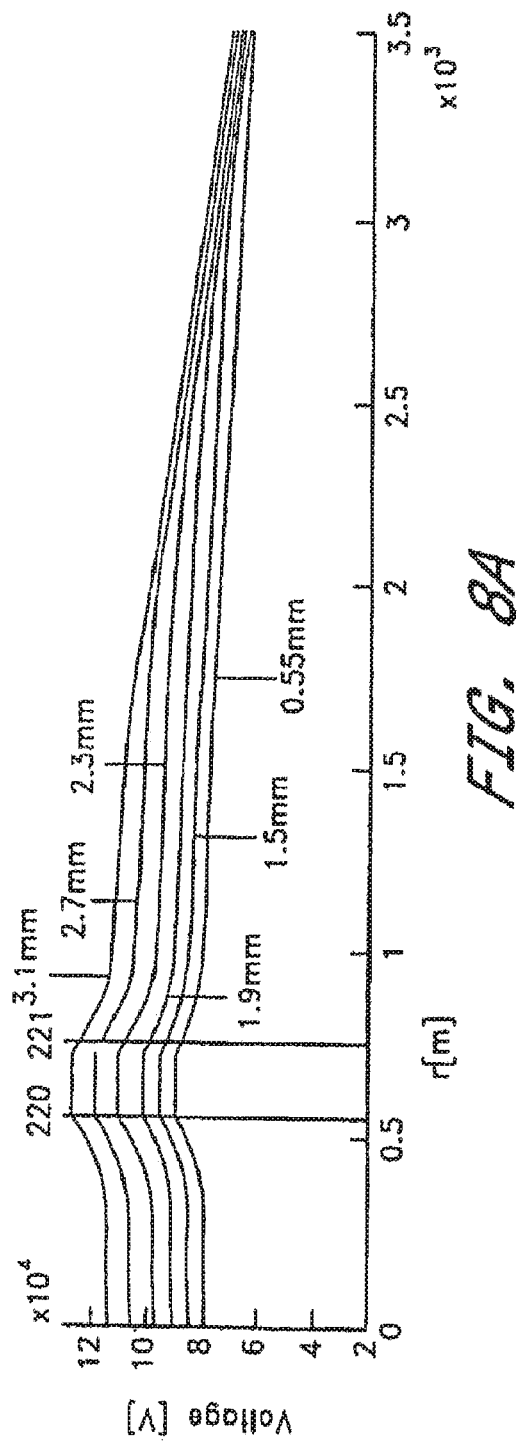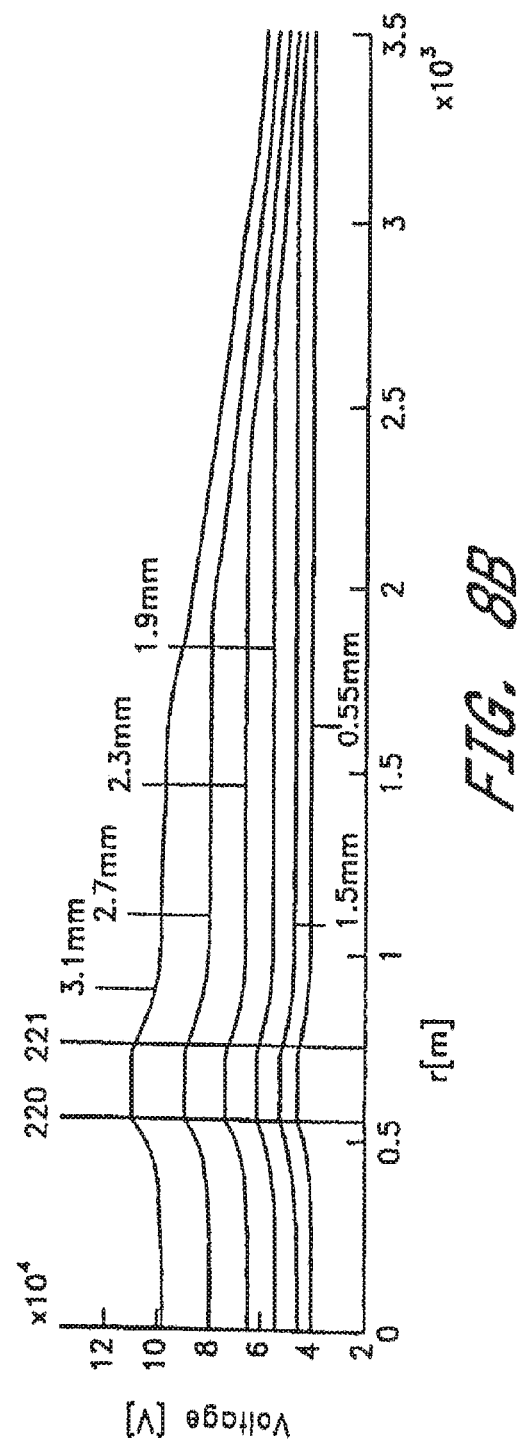

IMPEDANCE DEVICES AND METHODS OF USING THE SAME TO OBTAIN LUMINAL ORGAN MEASUREMENTS

PRIORITY

The present patent application a) is related to, claims the priority benefit of, and is a U.S. continuation patent application of, U.S. patent application Ser. No. 14/215,012, filed Mar. 16, 2014 and issued as U.S. Pat. No. 9,462,960 on Oct. 11, 2016, which is related to, and claims the priority benefit of, U.S. Provisional Patent Application Ser. No. 61/800,407, filed on Mar. 15, 2013; b) is related to, claims the priority benefit of, and is a continuation-in-part application of, U.S. patent application Ser. No. 14/755,096, filed Jun. 30, 2015, which is related to, claims the priority benefit of, and is a continuation application of, U.S. patent application Ser. No. 13/324,222, filed on Dec. 13, 2011 and issued as U.S. Pat. No. 9,066,708 on Jun. 30, 2015, which is related to, claims the priority benefit of, and is a continuation application of, U.S. patent application Ser. No. 12/098,242, filed on Apr. 4, 2008 and issued as U.S. Pat. No. 8,078,274 on Dec. 13, 2011, which is related to, claims the priority benefit of, and is a continuation-in-part application of, U.S. patent application Ser. No. 11/891,981, filed Aug. 14, 2007 and issued as U.S. Pat. No. 8,114,143 on Feb. 14, 2012, which is related to, claims the priority benefit of, and is a divisional application of, U.S. patent application Ser. No. 10/782,149, filed Feb. 19, 2004 and issued as U.S. Pat. No. 7,454,244 on Nov. 18, 2008, which is related to, claims the priority benefit of, U.S. Provisional Patent Application Ser. No. 60/449,266, filed Feb. 21, 2003, U.S. Provisional Patent Application Ser. No. 60/493,145, filed Aug. 7, 2003, and U.S. Provisional Patent Application Ser. No. 60/502,139, filed Sep. 11, 2003; and c) is related to, claims the priority benefit of, and is a continuation-in-part application of, U.S. patent application Ser. No. 14/580,580, filed Dec. 23, 2014, which is related to, claims the priority benefit of, and is a continuation application of, U.S. patent application Ser. No. 13/372,573, filed on Feb. 14, 2012 and issued as U.S. Pat. No. 8,918,169 on Dec. 23, 2014, which is related to, claims the priority benefit of, and is a continuation application of, U.S. patent application Ser. No. 11/891,981, filed Aug. 14, 2007 and issued as U.S. Pat. No. 8,114,143 on Feb. 14, 2012, which has the priority referenced above. The contents of each of these applications and patents are hereby incorporated by reference in their entirety into this disclosure.

BACKGROUND

The disclosure of the present application relates generally to medical diagnostics and treatment equipment, and in particular, to devices, systems, and methods for measuring luminal cross-sectional area of blood vessels, heart valves and other hollow visceral organs.

Coronary Heart Disease

Coronary heart disease is caused by atherosclerotic narrowing of the coronary arteries. It is likely to produce angina pectoris, heart attack or both. Coronary heart disease caused 466,101 deaths in USA in 1997 and is the single leading cause of death in America today. Approximately, 12 million people alive today have a history of heart attack, angina pectoris or both. The break down for males and females is 49% and 51%, respectively. This year, an estimated 1.1 million Americans will have a new or recurrent coronary attack, and more than 40% of the people experiencing these attacks will die as a result. About 225,000 people a year die of coronary attack without being hospitalized. These are sudden deaths caused by cardiac arrest, usually resulting from ventricular fibrillation. More than 400,000 Americans and 800,000 patients world-wide undergo a non-surgical coronary artery interventional procedure each year. Although only introduced in the 1990s, in some laboratories intra-coronary stents are used in 90% of these patients.

Stents increase minimal coronary lumen diameter to a greater degree than percutaneous transluminal coronary angioplasty (PTCA) alone according to the results of two randomized trials using the Palmaz-Schatz stent. These trials compared two initial treatment strategies: stenting alone and PTCA with "stent backup" if needed. In the Stent Restenosis Study (STRESS) trial, there was a significant difference in successful angiographic outcome in favor of stenting (96.1% vs. 89.6%).

Intravascular Ultrasound

Currently intravascular ultrasound is the method of choice to determine the true diameter of the diseased vessel in order to size the stent correctly. The term "vessel," as used herein, refers generally to any hollow, tubular, or luminal organ, area, or space within a body. The tomographic orientation of ultrasound enables visualization of the full 360° circumference of the vessel wall and permits direct measurements of lumen dimensions, including minimal and maximal diameter and cross-sectional area. Information from ultrasound is combined with that obtained by angiography. Because of the latticed characteristics of stents, radiographic contrast material can surround the stent, producing an angiographic appearance of a large lumen, even when the stent struts are not in full contact with the vessel wall. A large observational ultrasound study after angio-graphically guided stent deployment revealed an average residual plaque area of 51% in a comparison of minimal stent diameter with reference segment diameter, and incomplete wall apposition was frequently observed. In this cohort, additional balloon inflations resulted in a final average residual plaque area of 34%, even though the final angiographic percent stenosis was negative (20.7%). These investigators used ultrasound to guide deployment.

However, using intravascular ultrasound as mentioned above requires a first step of advancement of an ultrasound catheter and then withdrawal of the ultrasound catheter before coronary angioplasty thereby adding additional time to the stent procedure. Furthermore, it requires an ultrasound machine. This adds significant cost and time and more risk to the procedure.

Aortic Stenosis

Aortic Stenosis (AS) is one of the major reasons for valve replacements in adult. AS occurs when the aortic valve orifice narrows secondary to valve degeneration. The aortic valve area is reduced to one fourth of its normal size before it shows a hemodynamic effect. Because the area of the normal adult valve orifice is typically 3.0 to 4.0 $cm^2$, an area 0.75-1.0 $cm^2$ is usually not considered severe AS. When stenosis is severe and cardiac output is normal, the mean trans-valvular pressure gradient is generally >50 mmHg. Some patients with severe AS remain asymptomatic, whereas others with only moderate stenosis develop symptoms. Therapeutic decisions, particularly those related to corrective surgery, are based largely on the presence or absence of symptoms.

The natural history of AS in the adult consists of a prolonged latent period in which morbidity and mortality are very low. The rate of progression of the stenotic lesion has been estimated in a variety of hemodynamic studies performed largely in patients with moderate AS. Cardiac catheterization and Doppler echocardiographic studies indicate that some patients exhibit a decrease in valve area of 0.1-0.3 $cm^2$ per year; the average rate of change is 0.12 $cm^2$ per year. The systolic pressure gradient across the valve may increase by as much as 10 to 15 mmHg per year. However, more than half of the reported patients showed little or no progression over a 3-9 year period. Although it appears that progression of AS can be more rapid in patients with degenerative calcific disease than in those with congenital or rheumatic disease, it is not possible to predict the rate of progression in an individual patient.

Eventually, symptoms of angina, syncope, or heart failure develop after a long latent period, and the outlook changes dramatically. After onset of symptoms, average survival is <2-3 years. Thus, the development of symptoms identifies a critical point in the natural history of AS.

Many asymptomatic patients with severe AS develop symptoms within a few years and require surgery. The incidence of angina, dyspnea, or syncope in asymptomatic patients with Doppler outflow velocities of 4 m/s has been reported to be as high as 38% after 2 years and 79% after 3 years. Therefore, patients with severe AS require careful monitoring for development of symptoms and progressive disease.

Indications for Cardiac Catheterization

In patients with AS, the indications for cardiac catheterization and angiography are to assess the coronary circulation (to confirm the absence of coronary artery disease) and to confirm or clarify the clinical diagnosis of AS severity. If echocardiographic data are typical of severe isolated. AS, coronary angiography may be all that is needed before aortic valve replacement (AVR). Complete left- and right-heart catheterization may be necessary to assess the hemodynamic severity of AS if there is a discrepancy between clinical and echocardiographic data or evidence of associated valvular or congenital disease or pulmonary hypertension.

The pressure gradient across a stenotic valve is related to the valve orifice area and transvalvular flow through Bernoulli's principle. Thus, in the presence of depressed cardiac output, relatively low pressure gradients are frequently obtained in patients with severe AS. On the other hand, during exercise or other high-flow states, systolic gradients can be measured in minimally stenotic valves. For these reasons, complete assessment of AS requires (1) measurement of transvalvular flow, (2) determination of the transvalvular pressure gradient, and (3) calculation of the effective valve area. Careful attention to detail with accurate measurements of pressure and flow is important, especially in patients with low cardiac output or a low transvalvular pressure gradient.

Problems with Current Aortic Valve Area Measurements

Patients with severe AS and low cardiac output are often present with only modest transvalvular pressure gradients (i.e., <30 mmHg). Such patients can be difficult to distinguish from those with low cardiac output and only mild to moderate AS. In both situations, the low-flow state and low pressure gradient contribute to a calculated effective valve area that can meet criteria for severe AS. The standard valve area formula (simplified Hakki formula which is valve area=cardiac output/[pressure gradient]$^{1/2}$) is less accurate and is known to underestimate the valve area in low-flow states; under such conditions, it should be interpreted with caution. Although valve resistance is less sensitive to flow than valve area, resistance calculations have not been proved to be substantially better than valve area calculations.

In patients with low gradient stenosis and what appears to be moderate to severe AS, it may be useful to determine the transvalvular pressure gradient and calculate valve area and resistance during a baseline state and again during exercise or pharmacological (i.e., dobutamine infusion) stress. Patients who do not have true, anatomically severe stenosis exhibit an increase in the valve area during an increase in cardiac output. In patients with severe AS, these changes may result in a calculated valve area that is higher than the baseline calculation but that remains in the severe range, whereas in patients without severe AS, the calculated valve area will fall outside the severe range with administration of dobutamine and indicate that severe AS is not present.

There are many other limitations in estimating aortic valve area in patients with aortic stenosis using echocardiography and cardiac catheterization. Accurate measurement of the aortic valve area in patients with aortic stenosis can be difficult in the setting of low cardiac output or concomitant aortic or mitral regurgitations. Concomitant aortic regurgitation or low cardiac output can overestimate the severity of aortic stenosis. Furthermore, because of the dependence of aortic valve area calculation on cardiac output, any under or overestimation of cardiac output will cause inaccurate measurement of valve area. This is particularly important in patients with tricuspid regurgitation. Falsely measured aortic valve area could cause inappropriate aortic valve surgery in patients who do not need it.

Other Visceral Organs

Visceral organs such as the gastrointestinal tract and the urinary tract serve to transport luminal contents (fluids) from one end of the organ to the other end or to an absorption site. The esophagus, for example, transports swallowed material from the pharynx to the stomach. Diseases may affect the transport function of the organs by changing the luminal cross-sectional area, the peristalsis generated by muscle, or by changing the tissue components. For example, strictures in the esophagus and urethra constitute a narrowing of the organ where fibrosis of the wall may occur. Strictures and narrowing can be treated with distension, much like the treatment of plaques in the coronary arteries.

BRIEF SUMMARY

The disclosure of the present application provides for a system for measuring cross-sectional areas and pressure gradients in luminal organs. The disclosure of the present application also provides a method and apparatus for measuring cross-sectional areas and pressure gradients in luminal organs, such as, for example, blood vessels, heart valves, and other visceral hollow organs.

The present disclosure provides for a system for measuring cross-sectional areas and pressure gradients in luminal organs. The present disclosure also comprises a method and apparatus for measuring cross-sectional areas and pressure gradients in luminal organs, such as, for example, blood vessels, heart valves, and other visceral hollow organs.

In one embodiment, the system comprises an impedance catheter capable of being introduced into a treatment site, a solution delivery source for injecting a solution through the catheter into the treatment site, a constant current source enabling the supply of constant electrical current to the treatment site, and a data acquisition system enabling the measurement of parallel conductance at the treatment site, whereby enabling calculation of cross-sectional area at the treatment site.

In one embodiment, the catheter further comprises an inflatable balloon along its longitudinal axis.

In one embodiment, the catheter further comprises a pressure transducer near the distal end of the catheter.

In one approach, a method of measuring the cross-sectional area of a targeted treatment site comprises: introducing an impedance catheter into a treatment site; providing constant electrical current to the treatment site; injecting a first solution of first compound; measuring a first conductance value at the treatment site; injecting a second solution of a second compound; measuring a second conductance value at the treatment site; calculating the cross-sectional area of the treatment site based on the first and second conductance values and the conductivities of the first and second compounds.

In one approach, a method of constructing a three-dimensional model of a treatment site that comprises: introducing an impedance catheter into a treatment site; measuring a first cross-sectional area at a first point; adjusting the position of the catheter; measuring a second cross-sectional area at a second point, and so on; constructing a three-dimensional model of the treatment site along the longitudinal axis based on multiple longitudinal cross-sectional area measurements.

According to at least one embodiment of a method for measuring a cross-sectional area of a targeted treatment site, the method comprises the steps of introducing a device into a treatment site; injecting a known volume of a first solution having a first concentration and a first conductivity and injecting a known volume of a second solution having a second concentration and a second conductivity at a first position of the treatment site; measuring a first treatment site conductance at the first position of the treatment site; moving the device to a second position of the treatment site at a first speed; injecting a known volume of a first solution having a first concentration and a first conductivity and injecting a known volume of a second solution having a second concentration and a second conductivity at the second position of the treatment site; measuring a second treatment site conductance at the second position of the treatment site; and calculating cross-sectional areas of the first position and the second position of the treatment site.

In another embodiment, the treatment site comprises a site selected from the group consisting of a body lumen, a body vessel, a biliary tract, and an esophagus. In yet another embodiment, the treatment site comprises an esophagus, and wherein the step of injecting a known volume of a first solution having a first concentration and a first conductivity comprises the step of administering said first solution to a patient orally. In an additional embodiment, the first solution is NaCl.

According to at least one embodiment of a method for measuring a cross-sectional area of a targeted treatment site, the method further comprises the step of providing electrical current flow for a period of time to the treatment site through the device. In another embodiment, the first concentration of the first solution does not equal the second concentration of the second solution. In yet another embodiment, the first conductivity of the first solution does not equal the second conductivity of the second solution. In an additional embodiment, the method further comprises the step of calculating a first nodal voltage and a first electrical field based upon the first treatment site conductance value and a first current density. In yet an additional embodiment, the method further comprises the step of applying finite element analysis to the first nodal voltage and the first electrical field, wherein the step of finite element analysis is performed using a finite element software package.

According to at least one embodiment of a method for measuring a cross-sectional area of a targeted treatment site, the device comprises a catheter. In another embodiment, the catheter comprises an impedance catheter. In yet another embodiment, the catheter comprises a guide catheter.

According to at least one embodiment of a method for measuring a cross-sectional area of a targeted treatment site, the device comprises a wire. In another embodiment, the wire comprises an impedance wire. In yet another embodiment, the wire comprises a wire selected from the group consisting of a guide wire, a pressure wire, and a flow wire. In an additional embodiment, the wire comprises a flow wire, and wherein the flow wire is operable to measure a velocity of fluid flow.

According to at least one embodiment of a method for measuring a cross-sectional area of a targeted treatment site, the device comprises an inflatable balloon positioned along a longitudinal axis of the device. In another embodiment, the method further comprises the step of inflating the balloon to breakup materials causing stenosis at the treatment site. In yet another embodiment, the device further comprises a stent located over the balloon, the stent capable of being distended to a desired size and implanted into the treatment site. In an additional embodiment, the method further comprises the steps of distending the stent by inflating the underlying balloon; and releasing and implanting the stent into the treatment site. In yet an additional embodiment, the balloon is inflated using a fluid, and the method further comprises the steps of providing electrical current into the fluid filling the balloon at various degrees of balloon distension; measuring a conductance of the fluid inside the balloon; and calculating a cross-sectional area of the balloon lumen.

According to at least one embodiment of a method for measuring a cross-sectional area of a targeted treatment site, the method further comprises the steps of selecting an appropriately-sized stent based on a cross-sectional area of the treatment site; and implanting the stent into the treatment site. In another embodiment, the device comprises a pressure transducer. In yet another embodiment, the method further comprising the steps of measuring a first pressure gradient from the pressure transducer near the treatment site; and calculating the cross-sectional area of the treatment site based in part on the first pressure gradient.

According to at least one embodiment of a method for measuring a cross-sectional area of a targeted treatment site, the step of injecting a known volume of a first solution having a first concentration and a first conductivity temporarily substantially displaces blood present at the treatment site. In another embodiment, the first solution is heated to an internal body temperature of a body surrounding the treatment site prior to injection. In yet another embodiment, wherein the first solution and the second solution are heated to a common temperature prior to injection. In an additional embodiment, the first volume of the first solution is equal to the second volume of the second solution.

According to at least one embodiment of a method for measuring a cross-sectional area of a targeted treatment site, the step of measuring a first treatment site conductance further comprises the step of measuring a first cross-sectional area, and wherein the step of measuring a second treatment site conductance further comprises the step of measuring a second cross-sectional area. In another embodiment, the method further comprises the step of constructing a profile of the treatment site based in part on the measurements of the first cross-sectional area and the second cross-sectional area. In yet another embodiment, the step of moving the device comprises pulling back the device to a second position of the treatment site. In an additional embodiment, the step of moving the device comprises pushing the device forward to a second position of the treatment site.

According to at least one embodiment of a method for measuring a cross-sectional area of a targeted treatment site, the calculation of the cross-sectional areas of the first position and the second position of the treatment site is based in part upon the first treatment site conductance, the second treatment site conductance, the first conductivity of the first solution, and the second conductivity of the second solution. In another embodiment, the method further comprises the step of calculating two Coeff ratios based in part upon the first treatment site conductance, the second treatment site conductance, and the cross-sectional areas of the first position and the second position of the treatment site. In yet another embodiment, the step of moving the device to a second position of the treatment site further comprises the steps of obtaining one or more additional conductance measurements between the first position and the second position of the treatment site; and calculating one or more additional cross-sectional areas based upon the one or more additional conductance measurements. In an additional embodiment, the method further comprises the step of determining one or more diameters based in part upon the cross-sectional areas of the first position and the second position of the treatment site and the one or more additional cross-sectional areas based upon the additional conductance measurements.

According to at least one embodiment of a method for measuring a cross-sectional area of a targeted treatment site, the method further comprises the step of constructing a profile of the treatment site based upon the one or more diameters. In another embodiment, the method further comprises the step of calculating total conductance for a distance between the first position and the second position of the treatment site. In yet another embodiment, the method further comprises the step of constructing a profile of the treatment site based upon the cross-sectional areas. In an additional embodiment, the step of injecting a known volume of a first solution having a first concentration and a first conductivity comprises injecting the first solution local to the first position of the treatment site.

According to at least one embodiment of a method for measuring a cross-sectional area of a targeted treatment site, the device comprises a stent positioned along a longitudinal axis of the device, the stent capable of being distended to a desired size and implanted into the treatment site. In another embodiment, the method further comprises the steps of positioning the stent at or near the treatment site; distending the stent; and releasing and implanting the stent into the treatment site. In yet another embodiment, the method further comprises the step of introducing a stent at or near the treatment site, the stent having a length, a collapsed diameter, and a distended diameter. In an additional embodiment, a stent having a particular length is selected based upon a length of a stenosis. In yet an additional embodiment, the length of the stenosis is determined based upon a profile created in part based upon the cross-sectional areas of the first position and/or the second position of the treatment site.

According to at least one embodiment of a method for measuring a cross-sectional area of a targeted treatment site, a stent having a particular collapsed diameter is selected based upon the cross-sectional areas of the first position and/or the second position of the treatment site. In another embodiment, a stent having a particular distended diameter is selected based upon the cross-sectional areas of the first position and/or the second position of the treatment site. In yet another embodiment, the first treatment site conductance and the second treatment site conductance are retrieved by a data acquisition and processing system operably connected to the device, and wherein the data acquisition and processing system is operable to calculate cross-sectional areas.

According to at least one embodiment of a method for measuring a cross-sectional area of a targeted treatment site, the device comprises at least one suction/infusion port in communication with at least one lumen of the device, whereby said injections of solutions occur via the at least one suction/infusion port. In another embodiment, the device further comprises at least one solution delivery source operably coupled to the at least one lumen of the device, whereby the first solution and the second solution may be injected from the at least one solution delivery source through the at least one lumen of the device, through the at least one suction/infusion port, and into the treatment site. In yet another embodiment, the device comprises at least one excitation electrode and at least one detection electrode. In an additional embodiment, the at least one excitation electrode comprises a first excitation impedance lead, and wherein the at least one detection electrode comprises a first detection impedance lead.

According to at least one embodiment of a method for measuring a cross-sectional area of a targeted treatment site, the treatment site has a relative longitudinal axis, and wherein the method further comprises the step of constructing a profile along the relative longitudinal axis of the treatment site based in part on the first and second cross-sectional area measurements. In another embodiment, the treatment site has a relative longitudinal axis, and wherein the step of moving the device to a second position of the treatment site further comprises the steps of obtaining one or more additional conductance measurements between the first position and the second position of the treatment site; and calculating one or more additional cross-sectional areas based upon the one or more additional conductance measurements. In another embodiment, the method further comprises the step of constructing a profile along the relative longitudinal axis of the treatment site based in part on the first and second cross-sectional area measurements and the one or more additional cross-sectional areas. In yet another embodiment, the method further comprises the step of comprising the step of determining one or more diameters based in part upon the cross-sectional areas of the first position and the second position of the treatment site and the one or more additional cross-sectional areas based upon the additional conductance measurements. In an additional embodiment, the method further comprises the step of constructing a profile of the treatment site based upon the one or more diameters.

According to at least one embodiment of a method for measuring a cross-sectional area of a targeted treatment site, the device comprises a sensor for measurement of fluid flow. In another embodiment, the device is dimensioned so that a first solution can be infused therethrough. In yet another embodiment, the data acquisition and processing system is operable to receive conductance data from the device at a first treatment site, and wherein the data acquisition and processing system is further operable to determine the first treatment site conductance based in part from the conductance data.

According to at least one embodiment of a method for measuring a cross-sectional area of a targeted treatment site, the device comprises a catheter having a lumen, a proximal end, and a distal end, and wherein the at least one excitation electrode and the at least one detection electrode are positioned at or near the distal end of the catheter. In another embodiment, the at least one excitation electrode and the at least one detection electrode have insulated electrical wire connections that run through the lumen and proximal end of the catheter. In yet another embodiment, the at least one excitation electrode and the at least one detection electrode have electrical wire connections that are embedded within the catheter such that each wire comprising the electrical wire connections are insulated from the other wires.

According to at least one embodiment of a method for measuring a cross-sectional area of a targeted treatment site, the catheter comprises a lumen extending therethrough, and further comprising a wire positioned through at least a portion of the lumen of the catheter.

According to at least one embodiment of a method for measuring a cross-sectional area of a targeted treatment site, the method comprises the steps of introducing a device into a treatment site; injecting a known volume of a first solution having a first concentration and a first conductivity and injecting a known volume of a second solution having a second concentration and a second conductivity at a first position of the treatment site; measuring a first treatment site conductance at the first position of the treatment site; pulling back the device to a second position of the treatment site at a first speed while injecting a known volume of the second solution, wherein the second position is located proximally relative to the first position; injecting a known volume of a first solution having a first concentration and a first conductivity at the second position of the treatment site; measuring a second treatment site conductance at the second position of the treatment site; and calculating cross-sectional areas of the first position and the second position of the treatment site based in part upon the first treatment site conductance, the second treatment site conductance, the first conductivity of the first solution, and the second conductivity of the second solution. In another embodiment, the method further comprises the step of constructing a profile of the treatment site based in part on the measurements of the first cross-sectional area and the second cross-sectional area. In yet another embodiment, the device comprises an inflatable balloon along a longitudinal axis of the device.

According to at least one embodiment of a method for measuring a cross-sectional area of a targeted treatment site, the method further comprises the step of inflating the balloon to breakup any materials causing stenosis at the treatment site. In another embodiment, the device further comprises a stent located over the balloon, the stent capable of being distended to a desired lumen size and implanted into the treatment site. In yet another embodiment, the method further comprises the steps of distending the stent by inflating the underlying balloon; and releasing and implanting the stent into the treatment site. In an additional embodiment, the balloon is inflated using a fluid, and the method further comprises the steps of providing electrical current into the fluid filling the balloon at various degrees of balloon distension; measuring a conductance of the fluid inside the balloon; and calculating a cross-sectional area of the balloon lumen.

According to at least one embodiment of a method for measuring a cross-sectional area of a targeted treatment site, the method further comprises the steps of selecting an appropriately-sized stent based on a cross-sectional area of the treatment site; and implanting the stent into the treatment site. In another embodiment, the step of pulling back the device to a second position of the treatment site further comprises the step of obtaining one or more additional conductance measurements between the first position and the second position of the treatment site and the step of calculating one or more additional cross-sectional areas based upon the one or more additional conductance measurements. In yet another embodiment, the method further comprises the step of constructing a profile of the treatment site based in part upon the cross-sectional area of the first position and the second position of the treatment site and the one or more additional cross-sectional areas based upon the additional conductance measurements.

According to at least one embodiment of a method for measuring a cross-sectional area of a targeted treatment site, the method comprises the steps of calculating a total conductance based upon individual conductance values taken at a proximal end and a distal end of a segment; calculating two Coeff ratios based upon the total conductance and the cross-sectional areas of the proximal and the distal end of the segment; linearly interpolating along a length of pull back of a device for the Coeff so that the proximal and the distal end of the segment have the same Coeffs as calculated herein; calculating a total conductance for the length of the pull back; multiplying the total conductance for the length of the pull back by its respective Coeff for at least one point calculated during pull back to obtain a cross-sectional area for the at least one point calculated during pull back; and determining the diameter for the at least one point calculated during pull back from the cross-sectional area for the at least one point calculated during pull back.

In another embodiment, the step of calculating two Coeff ratios is performed by dividing the two cross-sectional areas by the total conductance. In yet another embodiment, the step of determining the diameter for the at least one point is determined by multiplying the cross-sectional area of the at least one point by four, dividing the resulting product by pi, and taking the square root of the resulting quotient.

According to at least one embodiment of a method for measuring a cross-sectional area of a targeted treatment site, the method comprises the steps of introducing a device into a treatment site; injecting a known volume of a first solution having a first concentration and a first conductivity at a first position of the treatment site; measuring a first conductance at the first position of the treatment site; injecting a known volume of a second solution having a second concentration and a second conductivity at a first position of the treatment site; measuring a second conductance at the first position of the treatment site; moving the device to a second position of the treatment site at a first speed; injecting a known volume of a first solution having a first concentration and a first conductivity at the second position of the treatment site; measuring a third conductance at the second position of the treatment site; injecting a known volume of a second solution having a second concentration and a second conductivity at the second position of the treatment site; measuring a fourth conductance at the second position of the treatment site; and calculating cross-sectional areas of the first position and the second position of the treatment site based in part from the first conductance, the second conductance, the third conductance, and the fourth conductance.

According to at least one embodiment of a method for constructing a profile of a targeted treatment site, the method comprises the steps of introducing a device into a treatment site; injecting a known volume of a first solution having a first concentration and a first conductivity and injecting a known volume of a second solution having a second concentration and a second conductivity at a first position of the treatment site; measuring a first treatment site conductance at the first position of the treatment site; moving the device to a second position of the treatment site at a first speed;

injecting a known volume of a first solution having a first concentration and a first conductivity and injecting a known volume of a second solution having a second concentration and a second conductivity at the second position of the treatment site; measuring a second treatment site conductance at the second position of the treatment site; calculating cross-sectional areas of the first position and the second position of the treatment site; and constructing a profile of the treatment site based upon the cross-sectional areas of the first position and the second position of the treatment site.

In another embodiment, the step of moving the device to a second position of the treatment site further comprises the steps of obtaining one or more additional conductance measurements between the first position and the second position of the treatment site; and calculating one or more additional cross-sectional areas based upon the one or more additional conductance measurements. In yet another embodiment, the method further comprises the step of constructing a profile of the treatment site based upon the cross-sectional areas of the first position and the second position of the treatment site and the one or more additional cross-sectional areas.

According to at least one embodiment of a method for implanting a stent to a targeted treatment site, the method comprises the steps of introducing a device into a treatment site; injecting a known volume of a first solution having a first concentration and a first conductivity and injecting a known volume of a second solution having a second concentration and a second conductivity at a first position of the treatment site; measuring a first treatment site conductance at the first position of the treatment site; moving the device to a second position of the treatment site at a first speed; injecting a known volume of a first solution having a first concentration and a first conductivity and injecting a known volume of a second solution having a second concentration and a second conductivity at the second position of the treatment site; measuring a second treatment site conductance at the second position of the treatment site; calculating cross-sectional areas of the first position and the second position of the treatment site; selecting an appropriately-sized stent based on a cross-sectional area of the treatment site; and implanting the stent into the treatment site.

The present disclosure also includes disclosure of exemplary unipolar, bipolar, and tetrapolar devices having various components, features, and/or configurations as described herein. The present disclosure also includes disclosure of exemplary unipolar, bipolar, and tripolar methods using one or more unipolar, bipolar, and tripolar devices.

The disclosure of the present application includes disclosure of exemplary unipolar, bipolar, and tripolar devices to perform one or more of the following procedures/tasks: (a) determining the size (cross-sectional area or diameter, for example) of a mammalian luminal organ, (b) determining parallel tissue conductance within a mammalian luminal organ, (c) navigation of said device(s) within a luminal organ, (d) determining the location of one or more body lumen junctions within a mammalian luminal organ, (e) determining profiles of a luminal organ, (f) ablating a tissue within a mammalian patient, (g) removing stenotic lesions from a vessel, (h) determining the existence, potential type, and/or vulnerability of a plaque within a luminal organ, (i) determining phasic cardiac cycle measurements, (j) determining vessel compliance, (k) determining the velocity of a fluid flowing through a mammalian luminal organ, (l) sizing valves using impedance and balloons, such as sizing a valve annulus for percutaneous valves, (m) detecting and/or removing contrast from mammalian luminal organs, (n) determining fractional flow reserve, and/or (o) placing leads within a mammalian luminal organ.

The present disclosure also includes disclosure of exemplary devices, such as exemplary unipolar, bipolar, tripolar, and tetrapolar devices to perform one or more of the following procedures/tasks: (a) ablation of relatively small veins for Endovascular Laser Therapy (EVLT) for treatment of venous insufficiency of varicose veins and/or other cosmetic procedures, and/or (b) navigation through a portion of a patient's urological system, such as within a ureter, to potentially identify a stenosis or a size abnormality.

In at least one embodiment of an impedance device of the present disclosure, the impedance device comprises an elongated body having a distal body end, and a first electrode located along the elongated body at or near the distal body end, the first electrode configured to obtain one or more conductance values within a mammalian luminal organ within an electric field, wherein a measured parameter of the mammalian luminal organ can be calculated based in part upon the one or more conductance values obtained by the first electrode. In another embodiment, the first electrode is configured to operate as an excitation electrode and a detection electrode. In yet another embodiment, the first electrode is configured to generate the electric field with an external electrode within a mammalian body when the external electrode that is not coupled to the elongated body is positioned upon or within the mammalian body and when the first electrode and the external electrode are activated. In an additional embodiment, the first electrode is configured to detect the electric field generated by the first electrode and the external electrode.

In at least one embodiment of an impedance device of the present disclosure, the impedance device further comprises a second electrode positioned along the elongated body, wherein the second electrode is configured to detect the electric field generated by the first electrode and the external electrode. In an additional embodiment, the first electrode is configured to generate the electric field with a first external electrode within a mammalian body when the first external electrode that is not coupled to the elongated body is positioned upon or within the mammalian body and when the first electrode and the external electrode are activated. In yet an additional embodiment, the second electrode is configured to detect the electric field with a second external electrode within the mammalian body when the second external electrode that is not coupled to the elongated body is positioned upon or within the mammalian body. In another embodiment, a known distance between the first electrode and the second electrode is between 0.5 mm and 1 mm, inclusive. In yet another embodiment, a known distance between the first electrode and the second electrode is between 0.5 mm and 1 mm, inclusive, and wherein the measured parameter is also calculated based in part upon the known distance.

In at least one embodiment of an impedance device of the present disclosure, the first electrode is configured to generate the electric field with an external electrode within a mammalian body when the external electrode that is not coupled to the elongated body is positioned upon or within the mammalian body and when the first electrode and the external electrode are activated. In another embodiment, the device further comprises a second electrode and a third electrode each positioned along the elongated body, the second electrode and the third electrode configured to detect the electric field generated by the first electrode and the external electrode.

In at least one embodiment of an impedance system of the present disclosure, the system comprises an elongated body having a distal body end and a first electrode located along the elongated body at or near the distal body end, the first electrode configured to obtain one or more conductance values within a mammalian luminal organ within an electric field, and a first external electrode that is not coupled to the elongated body, wherein a measured parameter of the mammalian luminal organ can be calculated based in part upon the one or more conductance values obtained by the first electrode within the electric field generated by the first electrode and the first external electrode. In an additional embodiment, the first electrode and the first external electrode are each configured to operate as an excitation electrode and a detection electrode. In yet an additional embodiment, the first external electrode comprises part of device selected from the group consisting of a patch, a sheath, and a clip. In another embodiment, the system further comprises a second electrode positioned along the elongated body, wherein the second electrode is configured to detect the electric field.

In at least one embodiment of an impedance system of the present disclosure, the system further comprises a second external electrode that is not coupled to the elongated body, wherein the second electrode and the second external electrode are configured to detect the electric field within a mammalian body when the second external electrode is positioned upon or within the mammalian body. In an additional embodiment, the system further comprises a third electrode positioned along the elongated body, wherein the third electrode is configured to detect the electric field with the second electrode.

In at least one embodiment of a method of using an impedance device of the present disclosure, the method comprises the steps of introducing at least part of an impedance device into a mammalian luminal organ at a first location, the impedance device comprising an elongated body having a distal body end, and a first electrode located along the elongated body at or near the distal body end, the first electrode configured to obtain one or more conductance values within a mammalian luminal organ within an electric field, providing electrical current to the first electrode and a first external electrode not coupled to the elongated body to generate the electric field, the first external electrode positioned upon or within a mammalian body having the mammalian luminal organ, obtaining at least one conductance value using the impedance device within the electric field, and calculating a measured parameter of the mammalian luminal organ based in part upon the at least one conductance value. In another embodiment, the measured parameter is selected from the group consisting of a luminal organ diameter and a luminal organ cross-sectional area, and wherein the step of obtaining is performed in the presence of a bolus of an injected fluid having a known conductivity different than that of blood. In yet another embodiment, the impedance device further comprises a second electrode positioned along the elongated body, and wherein the step of obtaining the at least one conductance value is performed using first electrode and the second electrode. In an additional embodiment, the impedance device further comprises a second electrode and a third electrode each positioned along the elongated body, and wherein the step of obtaining the at least one conductance value is performed using second electrode and the third electrode.

In at least one embodiment of a method of using an impedance device of the present disclosure, the step of obtaining at least one conductance value is performed within an undiluted bolus of an injected first solution having a known conductivity differing from a blood conductivity, and wherein the step of obtaining the at least another conductance value also performed within a bolus selected from the undiluted bolus of the injected first solution and an undiluted bolus of an injected second solution having a known conductivity differing from the blood conductivity. In another embodiment, the step of obtaining is performed when the first electrode is at a first location within the mammalian luminal organ, and wherein the method further comprises the following steps to be performed after the step of obtaining the at least one conductance value: moving the first electrode of the impedance device to a second location within the mammalian luminal organ, obtaining at least another conductance value using the impedance device within a field selected from the group consisting of the electric field and a second electric field, and calculating a second measured parameter of the mammalian luminal organ based in part upon the at least another conductance value. In an additional embodiment, the method further comprises the step of constructing a profile of the mammalian luminal organ based in part upon the measured parameter and the second measured parameter.

In at least one embodiment of a method of using an impedance device of the present disclosure, the step of introducing at least part of an impedance device into the mammalian luminal organ comprises introducing the impedance device selected from the group consisting of an impedance wire and an impedance catheter into the mammalian luminal organ. In another embodiment, the method further comprises the following steps to be performed after the step of obtaining the at least another conductance value: moving the first electrode of the impedance device to a third location within the mammalian luminal organ, and obtaining at least an additional conductance value using the impedance device within a field selected from the group consisting of the electric field, the second electric field, and a third electric field, calculating a third measured parameter of the mammalian luminal organ based in part upon the at least an additional conductance value, and constructing an additional profile of the mammalian luminal organ based in part upon the measured parameter, the second measured parameter, and the third measured parameter. In yet another embodiment, the method further comprises the step of inflating a balloon coupled to the impedance device to breakup materials causing a stenosis within the mammalian luminal organ. In an additional embodiment, the method further comprises the step of implanting a stent into the mammalian luminal organ by inflating a balloon coupled to the impedance device. In yet an additional embodiment, the balloon is inflated using a fluid, and wherein the method further comprises the steps of providing electrical current into the fluid filling the balloon at various degrees of balloon distension, measuring a conductance of the fluid inside the balloon, and calculating a cross-sectional area of a balloon lumen.

In at least one embodiment of a method of using an impedance device of the present disclosure, the method further comprises the step of measuring a velocity of fluid flow through the mammalian luminal organ using the impedance device. In an additional embodiment, the method further comprises the steps of measuring a first pressure gradient in the mammalian luminal organ using a pressure transducer coupled to the impedance device, and calculating a cross-sectional area of the mammalian luminal organ based in part on the first pressure gradient. In yet an additional embodiment, the method further comprises the step of determining a length of a stenosis present within the mammalian luminal organ based upon the profile.

In at least one embodiment of a method of using an impedance device of the present disclosure, the method comprises the steps of introducing at least part of an impedance device into a mammalian luminal organ at a first location, the impedance device comprising an elongated body having a distal body end, and a first electrode located along the elongated body at or near the distal body end, the first electrode configured to obtain one or more conductance values within a mammalian luminal organ within an electric field, providing electrical current to the first electrode and a first external electrode not coupled to the elongated body to generate the electric field, the first external electrode positioned upon or within a mammalian body having the mammalian luminal organ, obtaining at least one conductance value using the impedance device within the electric field and within an undiluted bolus of an injected first solution having a known conductivity differing from a blood conductivity, and calculating a measured parameter of the mammalian luminal organ based in part upon the at least one conductance value. In another embodiment, the impedance device further comprises a second electrode positioned along the elongated body, and wherein the step of obtaining the at least one conductance value is performed using first electrode and the second electrode. In yet another embodiment, the impedance device further comprises a second electrode and a third electrode each positioned along the elongated body, and wherein the step of obtaining the at least one conductance value is performed using second electrode and the third electrode.

In at least one embodiment of a method of using an impedance device of the present disclosure, the step of obtaining is performed when the first electrode is at a first location within the mammalian luminal organ, and wherein the method further comprises the following steps to be performed after the step of obtaining the at least one conductance value: moving the first electrode of the impedance device to a second location within the mammalian luminal organ, obtaining at least another conductance value using the impedance device within a field selected from the group consisting of the electric field and a second electric field, the step of obtaining the at least another conductance value also performed within a bolus selected from the undiluted bolus of the injected first solution and an undiluted bolus of an injected second solution having a known conductivity differing from the blood conductivity, and calculating a second measured parameter of the mammalian luminal organ based in part upon the at least another conductance value. In an additional embodiment, the method further comprises the step of constructing a profile of the mammalian luminal organ based in part upon the measured parameter and the second measured parameter. In yet an additional embodiment, the step of introducing at least part of an impedance device into the mammalian luminal organ comprises introducing the impedance device selected from the group consisting of an impedance wire and an impedance catheter into the mammalian luminal organ. In another embodiment, the method further comprises the following steps to be performed after the step of obtaining the at least another conductance value: moving the first electrode of the impedance device to a third location within the mammalian luminal organ, and obtaining at least an additional conductance value using the impedance device within a field selected from the group consisting of the electric field, the second electric field, and a third electric field, calculating a third measured parameter of the mammalian luminal organ based in part upon the at least an additional conductance value, and constructing an additional profile of the mammalian luminal organ based in part upon the measured parameter, the second measured parameter, and the third measured parameter. In yet another embodiment, the method further comprises the step of inflating a balloon coupled to the impedance device to breakup materials causing a stenosis within the mammalian luminal organ.

In at least one embodiment of a method of using an impedance device of the present disclosure, the method further comprises the steps of implanting a stent into the mammalian luminal organ by inflating a balloon coupled to the impedance device. In an additional embodiment, the balloon is inflated using a fluid, and wherein the method further comprises the steps of providing electrical current into the fluid filling the balloon at various degrees of balloon distension, measuring a conductance of the fluid inside the balloon, and calculating a cross-sectional area of a balloon lumen. In yet an additional embodiment, the method further comprises the step of measuring a velocity of fluid flow through the mammalian luminal organ using the impedance device. In another embodiment, the method further comprises the steps of measuring a first pressure gradient in the mammalian luminal organ using a pressure transducer coupled to the impedance device, and calculating a cross-sectional area of the mammalian luminal organ based in part on the first pressure gradient. In yet another embodiment, the method further comprises the step of determining a length of a stenosis present within the mammalian luminal organ based upon the profile.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 1A illustrates a balloon catheter having impedance measuring electrodes supported in front of the stenting balloon;

FIG. 1B illustrates a balloon catheter having impedance measuring electrodes within and in front of the balloon;

FIG. 1C illustrates a catheter having an ultrasound transducer within and in front of balloon;

FIG. 1D illustrates a catheter without a stenting balloon;

FIG. 1E illustrates a guide catheter with wire and impedance electrodes;

FIG. 1F illustrates a catheter with multiple detection electrodes;

FIG. 8A illustrates the voltage recorded by a conductance catheter with a radius of 0.55 mm for various size vessels (vessel radii of 3.1, 2.7, 2.3, 1.9, 1.5 and 0.55 mm for the six curves, respectively) when a 0.5% NaCl bolus is injected into the treatment site;

FIG. 8B illustrates the voltage recorded by a conductance catheter with a radius of 0.55 mm for various size vessels (vessel radii of 3.1, 2.7, 2.3, 1.9, 1.5 and 0.55 mm for the six curves, respectively) when a 1.5% NaCl bolus is injected into the treatment site;

Figure 2B:
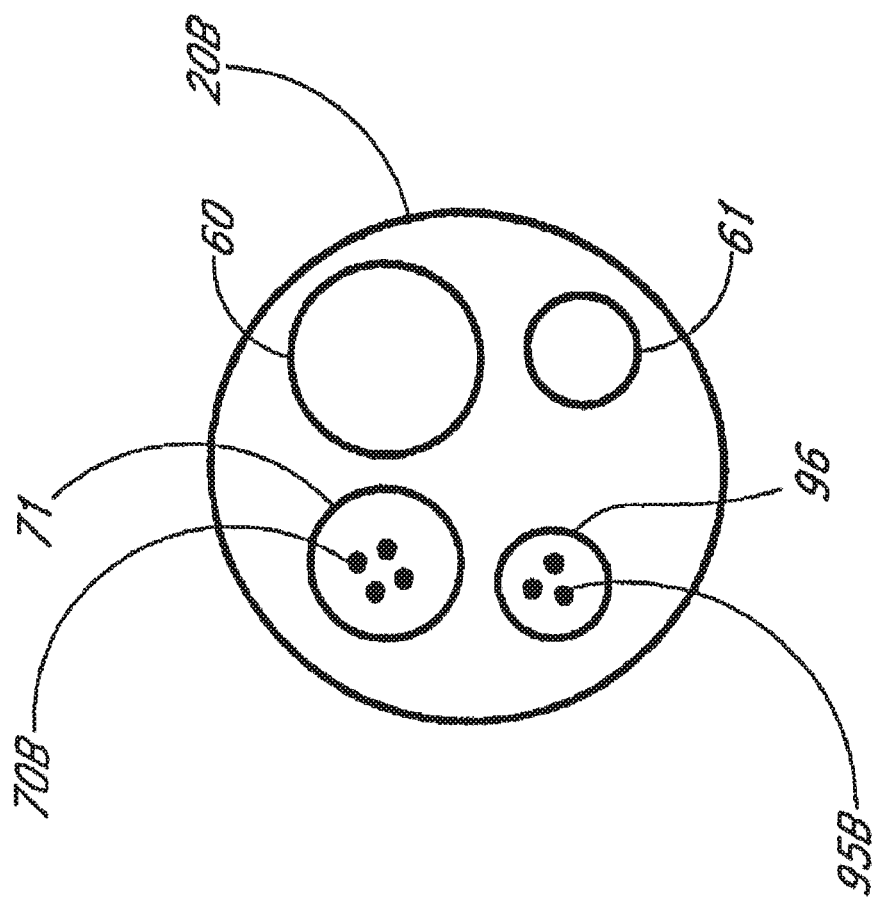
FIG. 2B illustrates a catheter in cross-section proximal to the location of the sensors showing the leads run in separate lumens.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

The disclosure of the present application provides devices, systems, and methods to obtain accurate measures of the luminal cross-sectional area of organ stenosis within acceptable limits to enable accurate and scientific stent sizing and placement in order to improve clinical outcomes by avoiding under or over deployment and under or over sizing of a stent which can cause acute closure or in-stent re-stenosis. For the purposes of promoting an understanding of the principles of the present disclosure, reference will now be made to the embodiments illustrated in the drawings, and specific language will be used to describe the same. It will nevertheless be understood that no limitation of the scope of the present disclosure is thereby intended.

In one embodiment, an angioplasty or stent balloon includes impedance electrodes supported by the catheter in front of the balloon. These electrodes enable the immediate measurement of the cross-sectional area of the vessel during the balloon advancement. This provides a direct measurement of non-stenosed area and allows the selection of the appropriate stent size. In one approach, error due to the loss of current in the wall of the organ and surrounding tissue is corrected by injection of two solutions of NaCl or other solutions with known conductivities. In another embodiment impedance electrodes are located in the center of the balloon in order to deploy the stent to the desired cross-sectional area. These embodiments and procedures substantially improve the accuracy of stenting and the outcome and reduce the cost.

Other embodiments make diagnosis of valve stenosis more accurate and more scientific by providing a direct accurate measurement of cross-sectional area of the valve annulus, independent of the flow conditions through the valve. Other embodiments improve evaluation of cross-sectional area and flow in organs like the gastrointestinal tract and the urinary tract.

Embodiments of the disclosure of the present application overcome the problems associated with determination of the size (cross-sectional area) of luminal organs, such as, for example, in the coronary arteries, carotid, femoral, renal and iliac arteries, aorta, gastrointestinal tract, urethra and ureter. Embodiments also provide methods for registration of acute changes in wall conductance, such as, for example, due to edema or acute damage to the tissue, and for detection of muscle spasms/contractions.

As described below, in one preferred embodiment, there is provided an angioplasty catheter with impedance electrodes near the distal end 19 of the catheter (i.e., in front of the balloon) for immediate measurement of the cross-sectional area of a vessel lumen during balloon advancement. This catheter includes electrodes for accurate detection of organ luminal cross-sectional area and ports for pressure gradient measurements. Hence, it is not necessary to change catheters such as with the current use of intravascular ultrasound. In one preferred embodiment, the catheter provides direct measurement of the non-stenosed area, thereby allowing the selection of an appropriately sized stent. In another embodiment, additional impedance electrodes may be incorporated in the center of the balloon on the catheter in order to deploy the stent to the desired cross-sectional area. The procedures described herein substantially improve the accuracy of stenting and improve the cost and outcome as well.

In another embodiment, the impedance electrodes are embedded within a catheter to measure the valve area directly and independent of cardiac output or pressure drop and therefore minimize errors in the measurement of valve area. Hence, measurements of area are direct and not based on calculations with underlying assumptions. In another embodiment, pressure sensors can be mounted proximal and distal to the impedance electrodes to provide simultaneous pressure gradient recording.

Devices

Exemplary impedance or conductance catheters for use within the disclosure of the present application are illustrated in FIGS. 1A-1F. With reference to the exemplary embodiment shown in FIG. 1A, four wires were threaded through one of the 2 lumens of a 4 Fr catheter. Here, electrodes 26 and 28, are spaced 1 mm apart and form the inner (detection) electrodes. Electrodes 25 and 27 are spaced 4-5 mm from either side of the inner electrodes and form the outer (excitation) electrodes. It can be appreciated that catheters of various sizes and including electrodes positioned in various locations may be useful in accordance with the present disclosure.

In one approach, dimensions of a catheter to be used for any given application depend on the optimization of the potential field using finite element analysis described below. For small organs, or in pediatric patients the diameter of the catheter may be as small as 0.3 mm. In large organs the diameter may be significantly larger depending on the results of the optimization based on finite element analysis. The balloon size will typically be sized according to the preferred dimension of the organ after the distension. The balloon may be made of materials, such as, for example, polyethylene, latex, polyestherurethane, or combinations thereof. The thickness of the balloon will typically be on the order of a few microns. The catheter will typically be made of PVC or polyethylene, though other materials may equally well be used. The excitation and detection electrodes typically surround the catheter as ring electrodes but they may also be point electrodes or have other suitable configurations. These electrodes may be made of any conductive material, preferably of platinum iridium or a carbon-coasted surface to avoid fibrin deposits. In a preferred embodiment, the detection electrodes are spaced with 0.5-1 mm between them and with a distance between 4-7 mm to the excitation electrodes on small catheters. The dimensions of the catheter selected for a treatment depend on the size of the vessel and are preferably determined in part on the results of finite element analysis, described below. On large catheters, for use in larger vessels and other visceral hollow organs, the electrode distances may be larger.

Referring to FIGS. 1A, 1B, 1C, and 1D, several embodiments of the catheters are illustrated. The catheters shown contain to a varying degree different electrodes, number and optional balloon(s). With reference to the embodiment shown in FIG. 1A, there is shown an impedance catheter 20 with 4 electrodes 25, 26, 27, and 28 placed close to the tip 19 of the catheter. Proximal to these electrodes is an angiography or stenting balloon 30 capable of being used for treating stenosis. Electrodes 25 and 27 are excitation electrodes, while electrodes 26 and 28 are detection electrodes, which allow measurement of cross-sectional area during advancement of the catheter, as described in further detail below. The portion of the catheter 20 within balloon 30 includes an infusion port 35 and a pressure port 36.

The catheter 20 may also advantageously include several miniature pressure transducers (not shown) carried by the catheter or pressure ports for determining the pressure gradient proximal at the site where the cross-sectional area is measured. The pressure is preferably measured inside the balloon and proximal, distal to and at the location of the cross-sectional area measurement, and locations proximal and distal thereto, thereby enabling the measurement of pressure recordings at the site of stenosis and also the measurement of pressure-difference along or near the stenosis. In one embodiment, shown in FIG. 1A, catheter 20 advantageously includes pressure port 90 and pressure port 91 proximal to or at the site of the cross-sectional measurement for evaluation of pressure gradients. As described below with reference to FIGS. 2A, 2B, and 3, in one embodiment, the pressure ports are connected by respective conduits in the catheter 20 to pressure sensors in the data acquisition system 100. Such pressure sensors are well known in the art and include, for example, fiber-optic systems, miniature strain gauges, and perfused low-compliance manometry.

In one embodiment, a fluid-filled silastic pressure-monitoring catheter is connected to a pressure transducer. Luminal pressure can be monitored by a low compliance external pressure transducer coupled to the infusion channel of the catheter. Pressure transducer calibration was carried out by applying 0 and 100 mmHg of pressure by means of a hydrostatic column.

In one embodiment, shown in FIG. 1B, the catheter 39 includes another set of excitation electrodes 40, 41 and detection electrodes 42, 43 located inside the angioplastic or stenting balloon 30 for accurate determination of the balloon cross-sectional area during angioplasty or stent deployment. These electrodes are in addition to electrodes 25, 26, 27, and 28.

In one embodiment, the cross-sectional area may be measured using a two-electrode system. In another embodiment, illustrated in FIG. 1F, several cross-sectional areas can be measured using an array of 5 or more electrodes. Here, the excitation electrodes 51, 52, are used to generate the current while detection electrodes 53, 54, 55, 56, and 57 are used to detect the current at their respective sites.

The tip of the catheter can be straight, curved or with an angle to facilitate insertion into the coronary arteries or other lumens, such as, for example, the biliary tract. The distance between the balloon and the electrodes is usually small, in the 0.5-2 cm range but can be closer or further away, depending on the particular application or treatment involved.

In another embodiment, shown in FIG. 1C, the catheter 21 has one or more imaging or recording devices, such as, for example, ultrasound transducers 50 for cross-sectional area and wall thickness measurements. As shown in this embodiment, the transducers 50 are located near the distal tip 19 of the catheter 21.

FIG. 1D illustrates an embodiment of impedance catheter 22 without an angioplastic or stenting balloon. The catheter in this exemplary embodiment also possesses an infusion or injection port 35 located proximal relative to the excitation electrode 25 and pressure port 36.

With reference to the embodiment shown in FIG. 1E, the electrodes 25, 26, 27, and 28 can also be built onto a wire 18, such as, for example, a pressure wire, and inserted through a guide catheter 23 where the infusion of bolus can be made through the lumen of the guide catheter 37.

With reference to the embodiments shown in FIGS. 1A, 1B, 1C, 1D, 1E, and 1F, the impedance catheter advantageously includes optional ports 35, 36, and 37 for suction of contents of the organ or infusion of fluid. The suction/infusion ports 35, 36, and 37 can be placed as shown with the balloon or elsewhere both proximal or distal to the balloon on the catheter. The fluid inside the balloon can be any biologically compatible conducting fluid. The fluid to inject through the infusion port or ports can be any biologically compatible fluid but the conductivity of the fluid is selected to be different from that of blood (e.g., NaCl).

In another embodiment (not illustrated), the catheter may contain an extra channel for insertion of a guide wire to stiffen the flexible catheter during the insertion or data recording. In yet another embodiment (not illustrated), the catheter may include a sensor for measurement of the flow of fluid in the body organ.

System for Determining Cross-Sectional Area and Pressure Gradient

The operation of the impedance catheter 20 is as follows: With reference to the embodiment shown in FIG. 1A for electrodes 25, 26, 27, and 28, conductance of current flow through the organ lumen and organ wall and surrounding tissue is parallel; i.e., $$G(z, t) = \frac{CSA(z, t) \cdot C_b}{L} + G_p(z, t) \quad [1a]$$

where $G_p(z,t)$ is the effective conductance of the structure outside the bodily fluid (organ wall and surrounding tissue) at a given position, z, along the long axis of the organ at a given time, t, and $C_b$ is the electrical conductivity of the bodily fluid which for blood generally depends on the temperature, hematocrit and orientation and deformation of blood cells, and L is the distance between the detection electrodes. Equation [1a] can be rearranged to solve for cross sectional area CSA(t), with a correction factor, α, if the electric field is non-homogeneous, as $$CSA(z, t) = \frac{L}{\alpha C_b}[G(z, t) - G_p(z, t)] \quad [1b]$$

where α would be equal to 1 if the field were completely homogeneous. The parallel conductance, $G_p$, is an offset error that results from current leakage. $G_p$ would equal 0 if all of the current were confined to the blood and hence would correspond to the cylindrical model given by Equation [10]. In one approach, finite element analysis is used to properly design the spacing between detection and excitation electrodes relative to the dimensions of the vessel to provide a nearly homogenous field such that a can be considered equal to 1. Our simulations show that a homogenous or substantially homogenous field is provided by (1) the placement of detection electrodes substantially equidistant from the excitation electrodes and (2) maintaining the distance between the detection and excitation electrodes substantially comparable to the vessel diameter. In one approach, a homogeneous field is achieved by taking steps (1) and/or (2) described above so that α is equals 1 in the foregoing analysis.

At any given position, z, along the long axis of organ and at any given time, t, in the cardiac cycle, $G_p$ is a constant. Hence, two injections of different concentrations and/or conductivities of NaCl solution give rise to two equations:

$$C_1 \cdot CSA(z,t) + L \cdot G_p(z,t) = L \cdot G_1(z,t) \quad [2]$$

and $$C_2 \cdot CSA(z,t) + L \cdot G_p(z,t) = L \cdot G_2(z,t) \quad [3]$$

which can be solved simultaneously for CSA and $G_p$ as $$CSA(z, t) = L\frac{[G_2(z, t) - G_1(z, t)]}{[C_2 - C_1]} \quad [4]$$

and $$G_p(z, t) = \frac{[C_2 \cdot G_1(z, t) - C_1 \cdot G_2(z, t)]}{[C_2 - C_1]} \quad [5]$$

where subscript "1" and subscript "2" designate any two injections of different NaCl concentrations and/or conductivities. For each injection k, $C_k$ gives rise to $G_k$ which is measured as the ratio of the root mean square of the current divided by the root mean square of the voltage. The $C_k$ is typically determined through in vitro calibration for the various NaCl concentrations and/or conductivities. The concentration of NaCl used is typically on the order of 0.45 to 1.8%. The volume of NaCl solution is typically about 5 ml, but sufficient to displace the entire local vascular blood volume momentarily. The values of CSA(t) and $G_p$(t) can be determined at end-diastole or end-systole (i.e., the minimum and maximum values) or the mean thereof.

Once the CSA and $G_p$ of the vessel are determined according to the above embodiment, rearrangement of Equation [1a] allows the calculation of the electrical conductivity of blood in the presence of blood blow as $$C_b = \frac{L}{CSA(z, t)}[G(z, t) - G_p(z, t)] \quad [6]$$

In this way, Equation [1b] can be used to calculate the CSA continuously (temporal variation as for example through the cardiac cycle) in the presence of blood.

In one approach, a pull or push through is used to reconstruct the vessel along its length. During a long injection (e.g., 10-15 s), the catheter can be pulled back or pushed forward at constant velocity, U. Equation [1b] can be expressed as $$CSA(U \cdot t, t) = \frac{L}{C_b}[G(U \cdot t, t) - G_p(U \cdot (t, t)] \quad [7]$$

where the axial position, z, is the product of catheter velocity, U, and time, t; i.e., z=U·t.

For the two injections, denoted by subscript "1" and subscript "2", respectively, different time points $T_1$, $T_2$, etc., may be considered such that equation [7] can be written as $$CSA_1(U \cdot T_1, t) = \frac{L}{C_1}[G_1(U \cdot T_1, t) - G_{p1}(U \cdot T_1, t)] \quad [8a]$$

$$CSA_1(U \cdot T_1, t) = \frac{L}{C_2}[G_2(U \cdot T_1, t) - G_{p1}(U \cdot T_1, t)] \quad [8b]$$

and $$CSA_2(U \cdot T_2, t) = \frac{L}{C_1}[G_1(U \cdot T_2, t) - G_{p2}(U \cdot T_2, t)] \quad [9a]$$

$$CSA_2(U \cdot T_2, t) = \frac{L}{C_2}[G_2(U \cdot T_2, t) - G_{p2}(U \cdot T_2, t)] \quad [9b]$$

and so on. Each set of equations [8a], [8b] and [9a], [9b], etc. can be solved for $GSA_1$, $G_{p1}$ and $CSA_2$, $G_{p2}$, respectively. Hence, the CSA at various time intervals may be measured and hence of different positions along the vessel to reconstruct the length of the vessel. In one embodiment, the data on the CSA and parallel conductance as a function of longitudinal position along the vessel can be exported from an electronic spreadsheet, such as, for example, an Excel file, to AutoCAD where the software uses the coordinates to render a profile on the monitor.

For example, in one exemplary approach, the pull back reconstruction was made during a long injection where the catheter was pulled back at constant rate by hand. The catheter was marked along its length such that the pull back was made at 2 mm/sec. Hence, during a 10 second injection, the catheter was pulled back about 2 cm. The data was continuously measured and analyzed at every two second interval; i.e., at every 4 mm. Hence, six different measurements of CSA and $G_p$ were made which were used to reconstruct the CSA and $G_p$ along the length of the 2 cm segment, namely at 0 mm, 4 mm, 8 mm, 12 mm, 16 mm, and 20 mm.

Operation of the Impedance Catheter 39:

With reference to the embodiment shown in FIG. 1B, the voltage difference between the detection electrodes 42 and 43 depends on the magnitude of the current, I, multiplied by the distance, D, between the detection electrodes and divided by the conductivity, C, of the fluid and the cross-sectional area, CSA, of the artery or other organs into which the catheter is introduced. Since the current, I, the distance, L, and the conductivity, C, normally can be regarded as calibration constants, an inverse relationship exists between the voltage difference and the CSA as shown by the following equations:

$$\Delta V = \frac{I \cdot L}{C \cdot CSA} \quad [10a]$$

or $$CSA = \frac{G \cdot L}{C} \quad [10b]$$

where G is conductance expressed as the ratio of current to voltage, $I/\Delta V$. Equation [10] is identical to Equation [1b] if the parallel conductance through the vessel wall is neglected and surrounding tissue because the balloon material acts as an insulator. This is the cylindrical model on which the conductance method is used.

As described below with reference to FIGS. 2A, 2B, 3, 4, and 5, the excitation and detection electrodes are electrically connected to electrically conductive leads in the catheter for connecting the electrodes to the data acquisition system 100.

Figure 2A:
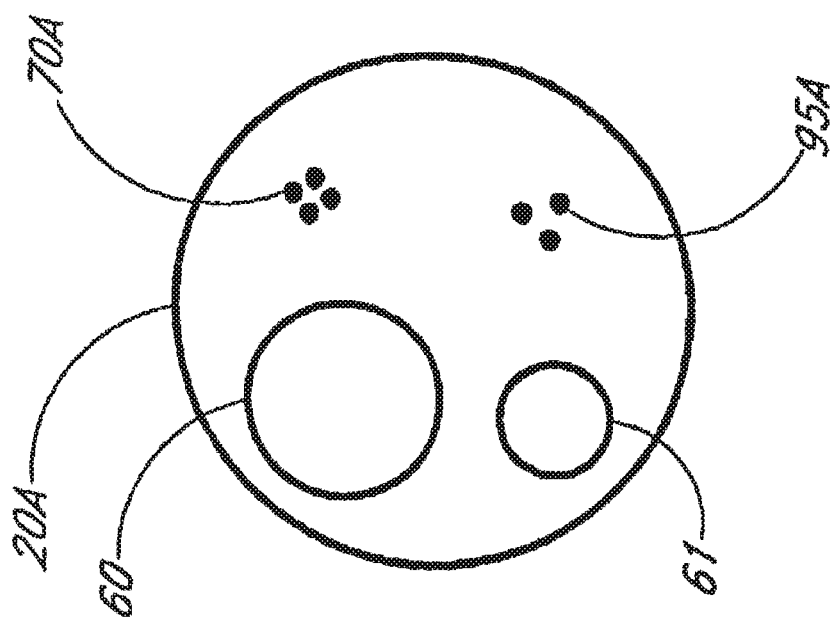
FIG. 2A illustrates a catheter in cross-section proximal to the location of the sensors showing the leads embedded in the material of the probe.

FIGS. 2A and 2B illustrate two embodiments 20A and 20B of the catheter in cross-section. Each embodiment has a lumen 60 for inflating and deflating the balloon and a lumen 61 for suction and infusion. The sizes of these lumens can vary in size. The impedance electrode electrical leads 70A are embedded in the material of the catheter in the embodiment in FIG. 2A, whereas the electrode electrical leads 70B are tunneled through a lumen 71 formed within the body of catheter 70B in FIG. 2B.

Pressure conduits for perfusion manometry connect the pressure ports 90, 91 to transducers included in the data acquisition system 100. As shown in FIG. 2A pressure conduits 95A may be formed in 20A. In another embodiment, shown in FIG. 2B, pressure conduits 95B constitute individual conduits within a tunnel 96 formed in catheter 20B. In the embodiment described above where miniature pressure transducers are carried by the catheter, electrical conductors will be substituted for these pressure conduits.

Figure 3:
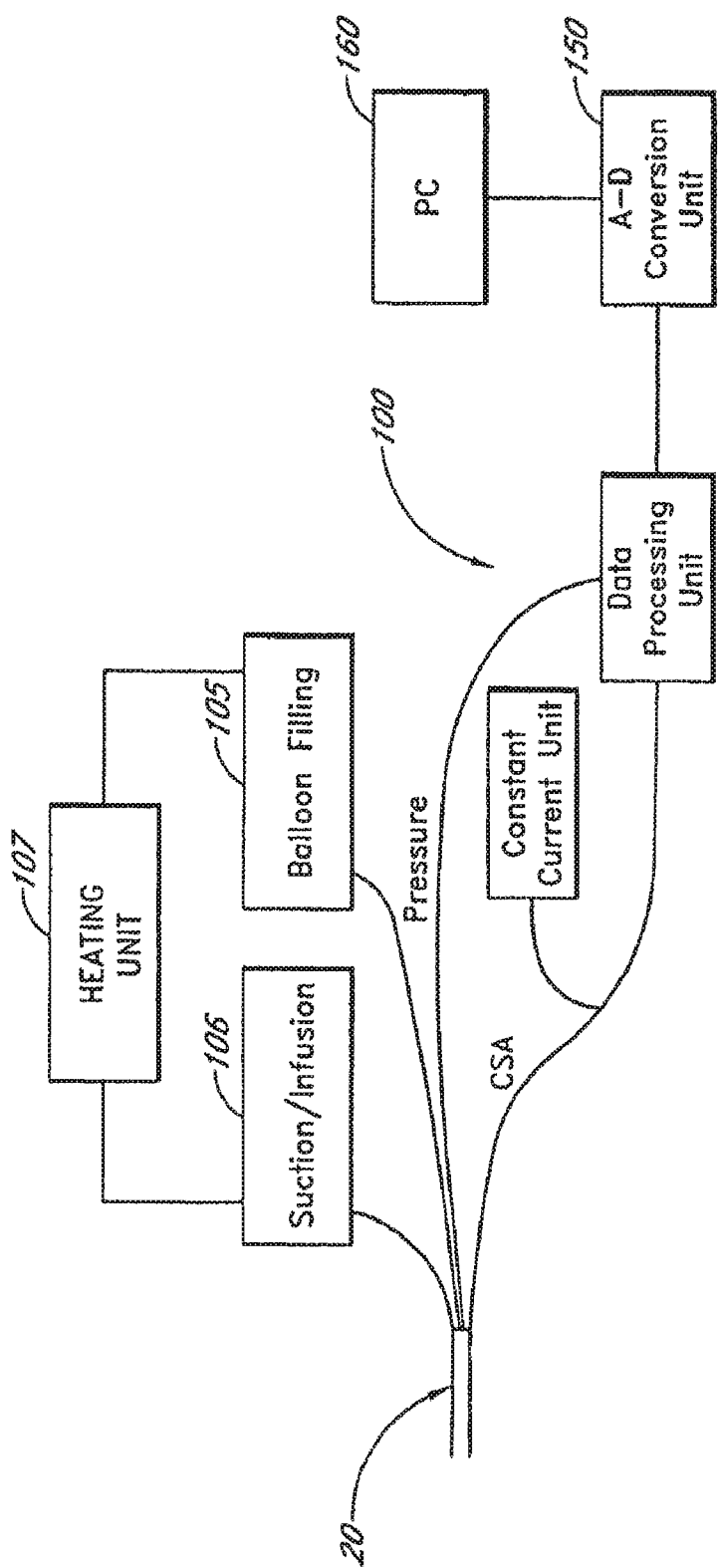
FIG. 3 is a schematic of one embodiment of the system showing a catheter carrying impedance measuring electrodes connected to the data acquisition equipment and excitation unit for the cross-sectional area measurement.

With reference to FIG. 3, in one exemplary embodiment, the catheter 20 connects to a data acquisition system 100, to a manual or automatic system 105 for distension of the balloon and to a system 106 for infusion of fluid or suction of blood. The fluid will be heated to 37-39° or equivalent to body temperature with heating unit 107. The impedance planimetry system typically includes a constant current unit, amplifiers and signal conditioners. The pressure system typically includes amplifiers and signal conditioners. The system can optionally contain signal conditioning equipment for recording of fluid flow in the organ.

In one preferred embodiment, the system is pre-calibrated and the probe is available in a package. Here, the package also preferably contains sterile syringes with the fluids to be injected. The syringes are attached to the machine and after heating of the fluid by the machine and placement of the probe in the organ of interest, the user presses a button that initiates the injection with subsequent computation of the desired parameters. The cross-sectional area, CSA, and parallel conductance, $G_p$, and other relevant measures such as distensibility, tension, etc. will typically appear on the display panel in the PC module 160. Here, the user can then remove the stenosis by distension or by placement of a stent.

If more than one CSA is measured, the system can contain a multiplexer unit or a switch between CSA channels. In one embodiment, each CSA measurement will be through separate amplifier units. The same may account for the pressure channels.

In one embodiment, the impedance and pressure data are analog signals which are converted by analog-to-digital converters 150 and transmitted to a computer 160 for on-line display, on-line analysis and storage. In another embodiment, all data handling is done on an entirely analog basis. The analysis advantageously includes software programs for reducing the error due to conductance of current in the organ wall and surrounding tissue and for displaying profile of the CSA distribution along the length of the vessel along with the pressure gradient. In one embodiment of the software, a finite element approach or a finite difference approach is used to derive the CSA of the organ stenosis taking parameters such as conductivities of the fluid in the organ and of the organ wall and surrounding tissue into consideration. In another embodiment, simpler circuits are used; e.g., based on making two or more injections of different NaCl solutions to vary the resistivity of fluid in the vessel and solving the two simultaneous Equations [2] and [3] for the CSA and parallel conductance (Equations [4] and [5], respectively). In another embodiment, the software contains the code for reducing the error in luminal CSA measurement by analyzing signals during interventions such as infusion of a fluid into the organ or by changing the amplitude or frequency of the current from the constant current amplifier. The software chosen for a particular application, preferably allows computation of the CSA with only a small error instantly or within acceptable time during the medical procedure.

In one approach, the wall thickness is determined from the parallel conductance for those organs that are surrounded by air or non-conducting tissue. In such cases, the parallel conductance is equal to $$G_p = \frac{CSA_w \cdot C_w}{L} \quad [11a]$$

where $CSA_w$ is the wall area of the organ and $C_w$ is the electrical conductivity through the wall. This equation can be solved for the wall $CSA_w$ as $$CSA_w = \frac{G_p \cdot L}{C_w} \quad [11b]$$

For a cylindrical organ, the wall thickness, h, can be expressed as $$h = \frac{CSA_w}{\pi D} \qquad [12]$$

where D is the diameter of the vessel which can be determined from the circular CSA ($D=[4\ CSA/\pi]^{1/2}$).

When the CSA, pressure, wall thickness, and flow data are determined according to the embodiments outlined above, it is possible to compute the compliance (e.g., $\Delta CSA/\Delta P$), tension (e.g., P·r, where P and r are the intraluminal pressure and radius of a cylindrical organ), stress (e.g., P·r/h where h is the wall thickness of the cylindrical organ), strain (e.g., $(C-C_d)/C_d$ where C is the inner circumference and $C_d$ is the circumference in diastole) and wall shear stress (e.g., $4\mu Q/r^3$ where $\mu$, Q and r are the fluid viscosity, flow rate and radius of the cylindrical organ, respectively, for a fully developed flow). These quantities can be used in assessing the mechanical characteristics of the system in health and disease.

Exemplary Method

In one approach, luminal cross-sectional area is measured by introducing a catheter from an exteriorly accessible opening (e.g., mouth, nose, or anus for GI applications; or e.g., mouth or nose for airway applications) into the hollow system or targeted luminal organ. For cardiovascular applications, the catheter can be inserted into the organs in various ways; e.g., similar to conventional angioplasty. In one embodiment, an 18 gauge needle is inserted into the femoral artery followed by an introducer. A guide wire is then inserted into the introducer and advanced into the lumen of the femoral artery. A 4 or 5 Fr conductance catheter is then inserted into the femoral artery via wire and the wire is subsequently retracted. The catheter tip containing the conductance electrodes can then be advanced to the region of interest by use of x-ray (i.e., fluoroscopy). In another approach, this methodology is used on small to medium size vessels (e.g., femoral, coronary, carotid, iliac arteries, etc.).

In one approach, a minimum of two injections (with different concentrations and/or conductivities of NaCl) are required to solve for the two unknowns, CSA and $G_p$. In another approach, three injections will yield three set of values for CSA and $G_p$ (although not necessarily linearly independent), while four injections would yield six set of values. In one approach, at least two solutions (e.g., 0.5% and 1.5% NaCl solutions) are injected in the targeted luminal organ or vessel. Our studies indicate that an infusion rate of approximately 1 ml/s for a five second interval is sufficient to displace the blood volume and results in a local pressure increase of less than 10 mmHg in the coronary artery. This pressure change depends on the injection rate which should be comparable to the organ flow rate.

In one preferred approach, involving the application of Equations [4] and [5], the vessel is under identical or very similar conditions during the two injections. Hence, variables, such as, for example, the infusion rate, bolus temperature, etc., are similar for the two injections. Typically, a short time interval is to be allowed (1-2 minute period) between the two injections to permit the vessel to return to homeostatic state. This can be determined from the baseline conductance as shown in FIG. 4 or 5. The parallel conductance is preferably the same or very similar during the two injections. In one approach, dextran, albumin or another large molecular weight molecule can be added to the NaCl solutions to maintain the colloid osmotic pressure of the solution to reduce or prevent fluid or ion exchange through the vessel wall.

In one approach, the NaCl solution is heated to body temperature prior to injection since the conductivity of current is temperature dependent. In another approach, the injected bolus is at room temperature, but a temperature correction is made since the conductivity is related to temperature in a linear fashion.

In one approach, a sheath is inserted either through the femoral or carotid artery in the direction of flow. To access the lower anterior descending (LAD) artery, the sheath is inserted through the ascending aorta. For the carotid artery, where the diameter is typically on the order of 5-5.5 mm, a catheter having a diameter of 1.9 mm can be used, as determined from finite element analysis, discussed further below. For the femoral and coronary arteries, where the diameter is typically in the range from 3.5-4 mm, so a catheter of about 0.8 mm diameter would be appropriate. The catheter can be inserted into the femoral, carotid or LAD artery through a sheath appropriate for the particular treatment. Measurements for all three vessels can be made similarly.

Described here are the protocol and results for one exemplary approach that is generally applicable to most arterial vessels. The conductance catheter was inserted through the sheath for a particular vessel of interest. A baseline reading of voltage was continuously recorded. Two containers containing 0.5% and 1.5% NaCl were placed in temperature bath and maintained at 37°. A 5-10 ml injection of 1.5% NaCl was made over a 5 second interval. The detection voltage was continuously recorded over a 10 second interval during the 5 second injection. Several minutes later, a similar volume of 1.5% NaCl solution was injected at a similar rate. The data was again recorded. Matlab was used to analyze the data including filtering with high pass and with low cut off frequency (1200 Hz). The data was displayed using Matlab and the mean of the voltage signal during the passage of each respective solution was recorded. The corresponding currents were also measured to yield the conductance, G=I/V. The conductivity of each solution was calibrated with six different tubes of known CSA at body temperature. A model using Equation [10] was fitted to the data to calculate conductivity C. The analysis was carried out in SPSS using the non-linear regression fit. Given C and G for each of the two injections, an excel sheet file was formatted to calculate the CSA and $G_p$ as per Equations [4] and [5], respectively. These measurements were repeated several times to determine the reproducibility of the technique. The reproducibility of the data was within 5%. Ultrasound (US) was used to measure the diameter of the vessel simultaneous with our conductance measurements. The detection electrodes were visualized with US and the diameter measurements was made at the center of the detection electrodes. The maximum differences between the conductance and US measurements were within 10%.

FIGS. 4A, 4B, 5A and 5B illustrate voltage measurements in the blood stream in the left carotid artery. Here, the data acquisition had a the sampling frequency of 75 KHz, with two channels—the current injected and the detected voltage, respectively. The current injected has a frequency of 5 KHz, so the voltage detected, modulated in amplitude by the impedance changing through the bolus injection will have a spectrum in the vicinity of 5 KHz.

Figure 4A:
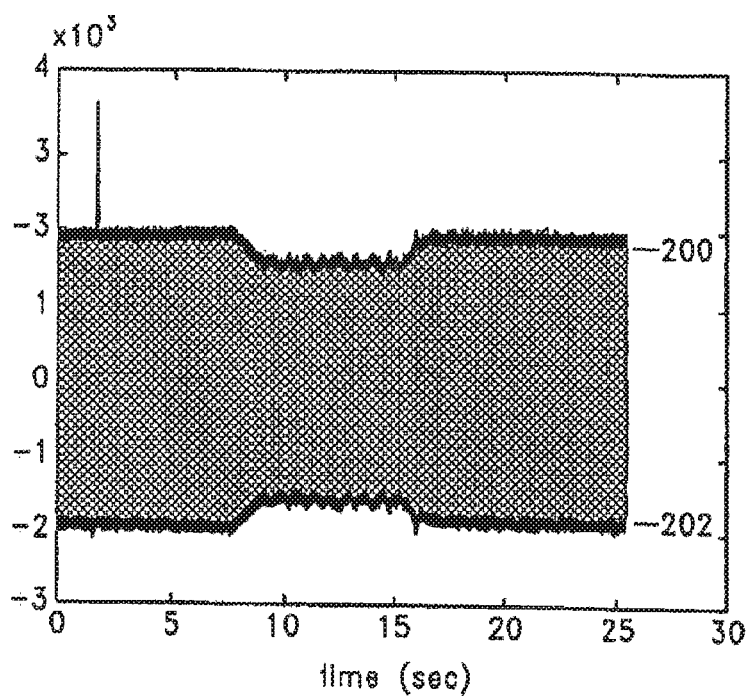
FIG. 4A show the detected filtered voltage drop as measured in the blood stream before and after injection of 1.5% NaCl solution.
Figure 4B:
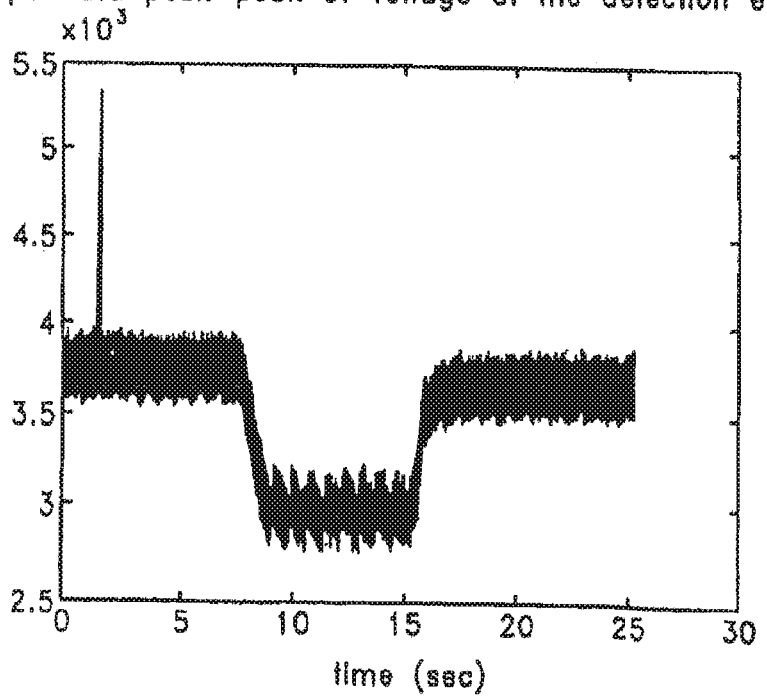
FIG. 4B shows the peak-to-peak envelope of the detected voltage shown in FIG. 4A.
Figure 5A:
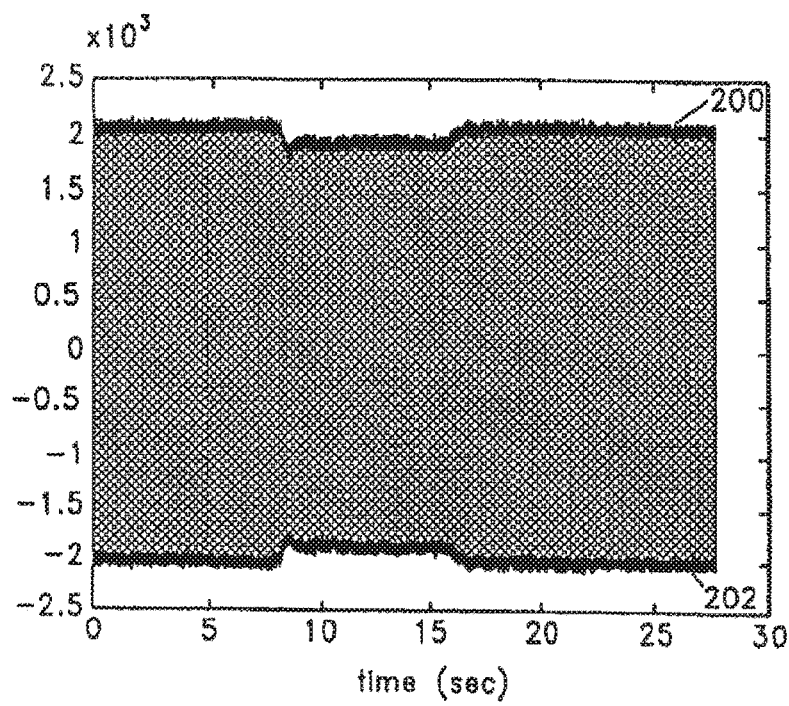
FIG. 5A show the detected filtered voltage drop as measured in the blood stream before and after injection of 0.5% NaCl solution.
Figure 5B:
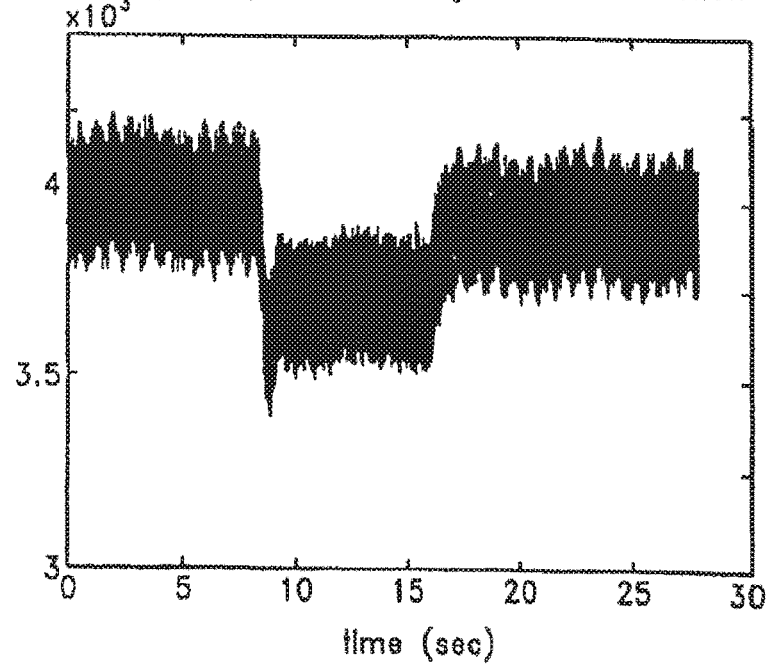
FIG. 5B shows the peak-to-peak envelope of the detected voltage shown in FIG. 5A.

With reference to FIG. 4A, there is shown a signal processed with a high pass filter with low cut off frequency (1200 Hz). The top and bottom portions 200, 202 show the peak-to-peak envelope detected voltage which is displayed in FIG. 4B (bottom). The initial 7 seconds correspond to the baseline; i.e., electrodes in the blood stream. The next 7 seconds correspond to an injection of hyper-osmotic NaCl solution (1.5% NaCl). It can be seen that the voltage is decreased implying increase conductance (since the injected current is constant). Once the NaCl solution is washed out, the baseline is recovered as can be seen in the last portion of the FIGS. 4A and 4B. FIGS. 5A and 5B shows similar data corresponding to 0.5% NaCl solutions.

The voltage signals are ideal since the difference between the baseline and the injected solution is apparent and systematic. Furthermore, the pulsation of vessel diameter can be seen in the 0.5% and 1.5% NaCl injections (FIGS. 4 and 5, respectively). This allows determination of the variation of CSA throughout the cardiac cycle as outline above.

The NaCl solution can be injected by hand or by using a mechanical injector to momentarily displace the entire volume of blood or bodily fluid in the vessel segment of interest. The pressure generated by the injection will not only displace the blood in the antegrade direction (in the direction of blood flow) but also in the retrograde direction (momentarily push the blood backwards). In other visceral organs which may be normally collapsed, the NaCl solution will not displace blood as in the vessels but will merely open the organs and create a flow of the fluid. In one approach, after injection of a first solution into the treatment or measurement site, sensors monitor and confirm baseline of conductance prior to injection of a second solution into the treatment site.

The injections described above are preferably repeated at least once to reduce errors associated with the administration of the injections, such as, for example, where the injection does not completely displace the blood or where there is significant mixing with blood. It will be understood that any bifurcation(s) (with branching angle near 90 degrees) near the targeted luminal organ can cause an overestimation of the calculated CSA. Hence, generally the catheter should be slightly retracted or advanced and the measurement repeated. An additional application with multiple detection electrodes or a pull back or push forward during injection will accomplish the same goal. Here, an array of detection electrodes can be used to minimize or eliminate errors that would result from bifurcations or branching in the measurement or treatment site.

In one approach, error due to the eccentric position of the electrode or other imaging device can be reduced by inflation of a balloon on the catheter. The inflation of balloon during measurement will place the electrodes or other imaging device in the center of the vessel away from the wall. In the case of impedance electrodes, the inflation of balloon can be synchronized with the injection of bolus where the balloon inflation would immediately precede the bolus injection. Our results, however, show that the error due to catheter eccentricity is small.

The CSA predicted by Equation [4] corresponds to the area of the vessel or organ external to the catheter (i.e., CSA of vessel minus CSA of catheter). If the conductivity of the NaCl solutions is determined by calibration from Equation [10] with various tubes of known CSA, then the calibration accounts for the dimension of the catheter and the calculated CSA corresponds to that of the total vessel lumen as desired. In one embodiment, the calibration of the CSA measurement system will be performed at 37° C. by applying 100 mmHg in a solid polyphenolenoxide block with holes of known CSA ranging from 7.065 mm² (3 mm in diameter) to 1017 mm² (36 mm in diameter). If the conductivity of the solutions is obtained from a conductivity meter independent of the catheter, however, then the CSA of the catheter is generally added to the CSA computed from Equation [4] to give the desired total CSA of the vessel.

The signals are generally non-stationary, nonlinear and stochastic. To deal with non-stationary stochastic functions, one can use a number of methods, such as the Spectrogram, the Wavelet's analysis, the Wigner-Ville distribution, the Evolutionary Spectrum, Modal analysis, or preferably the intrinsic model function (IMF) method. The mean or peak-to-peak values can be systematically determined by the aforementioned signal analysis and used in Equation [4] to compute the CSA.

Exemplary Four-Injection Approach

In at least one method of the disclosure of the present application, a four-injection approach is provided. As previously disclosed herein, two injections provide the cross-sectional area, CSA, and parallel conductance, $G_p$, at a particular point.

In at least one approach, four injections are provided to determine parallel conductance at multiple points. In an exemplary study, four injections may be performed to determine a segment of 2-3 cm long or longer. In this study, two injections may be performed at the distal end of the segment, and two injections may be performed at the proximal end of the segment. The two injections may deliver, for example, a volume of 1.5% NaCl and a volume of 0.5% NaCl, at each end of the segment, noting that any number of solutions, volumes, and concentrations thereof suitable for such a study, or for the other studies contemplated by the disclosure of the present application, could be utilized. For example, solutions having different salinities can be introduced in various physiological saline solutions (PSS) or in a Kreb solution containing other ions such as potassium, sodium, etc. In this exemplary study, the first two injections (1.5% NaCl and 0.5% NaCl) may be made at the distal point of the segment, and the catheter system would then be pulled back to the proximal point of the segment, whereby two more injections (1.5% NaCl and 0.5% NaCl) may be made, with conductance values taken at the distal end and the proximal end of the segment used to determine the entire profile of the segment.

As referenced herein with respect to Equation [1a], conductance may be calculated taking into account cross-sectional area, electrical conductivity of a fluid, and effective conductance of a structure. When performing a study as described above, the two end points (proximal and distal ends of a segment) are clearly exact, and an intermediate profile between those two points can be derived based upon the analysis provided herein. Since the cross-sectional area, CSA, and parallel conductance at a point, $G_p$, are known at each of the two ends of a segment, the corresponding blood conductivity may be calculated:

$$G_{Total} = \frac{CSA \cdot C_b}{L} + G_p \qquad [13a]$$

where $G_{Total}$ is the total conductance (current divided by voltage), CSA is the cross-sectional area, $C_b$ is the blood conductivity, L is the detection electrode spacing on the catheter, and $G_p$ is the parallel conductance at a point. The mean of the two values may then be calculated based upon the foregoing.

A procedure as described above may be accomplished, for example, by performing the following steps:

Step 1: Calculate total conductance ($G_{Total}$, current divided by voltage, or I/V, where I is the current injected and V is the voltage recorded) for two ends (proximal and distal) of a segment.

Step 2: Calculate the Coeff ratio (cross-sectional area divided by total conductance, or $CSA/G_{Total}$) at the two ends of the segment.

Step 3: Linearly interpolate along the length of the pull back for the Coeff, so that the two ends of the segment have the same Coeffs calculated from Step 2 above.

Step 4: Calculate total conductance ($G_{Total}$) for the entire length of the pull back (distance between the two ends of the segment).

Step 5: At each point calculated in the pull back, multiply the total conductance ($G_{Total}$) times its respective Coeff. The product of this calculation is the cross-sectional area (CSA).

Step 6: Determine the diameter from the cross-sectional area (CSA) along the entire profile.

A mathematical explanation of the concept referenced in the procedure above is as follows. First, the equation governing the physics of electrical conductance has the following form:

$$G_{Total} = \frac{I}{V} = \frac{CSA \cdot \sigma}{L} + G_p \quad [14]$$

where $G_{Total}$ is the total conductance, I is the current, V is the voltage, CSA is the cross-sectional area, $\sigma$ is the conductivity of the fluid, L is the detection electrode spacing on the catheter, and $G_p$ is the parallel conductance at a point.

Experimentation as shown that parallel conductance ($G_p$) is linearly related to cross-sectional area, with a negative slope. For example, a larger CSA has a smaller $G_p$. As such, $G_p$ can be replaced with a linear function of CSA as follows:

$$G_{Total} = \frac{I}{V} = \frac{CSA \cdot \sigma}{L} + m \cdot CSA + b \quad [15]$$

where $G_{Total}$ is the total conductance, I is the current, V is the voltage, CSA is the cross-sectional area, $\sigma$ is the conductivity of the fluid, L is the detection electrode spacing on the catheter, m is the slops, and b is the intercept as can be determined for a linear least square fit. This may be rearranged as follows:

$$G_{Total} = \left(\frac{\sigma}{L} + m\right) CSA + b \quad [16]$$

It is shown that total conductance ($G_{Total}$) is clearly linearly related to cross-sectional area (CSA). If the coefficient b is ignored (wherein b should be equal to zero if CSA is equal to zero), then we have the following:

$$\left(\frac{CSA}{G_{Total}}\right) = Coeff \quad [17]$$

The Coeff value at both ends of a segment can be found where the two injections are made, and those values may then be used to linearly interpolate across the profile. Once a Coeff value for every point in the pull back is determined, those Coeff values are multiplied by their respective $G_{Total}$ values to determine the CSA values along the profile, namely:

$$CSA = Coeff * G_{Total} \quad [18]$$

and $$Diameter = \sqrt{\frac{4 * CSA}{\pi}} \quad [19]$$

to determine a diameter.

Exemplary Three-Injection Approach

In at least one method of the disclosure of the present application, a three-injection approach to determine a profile as outlined above with respect to the four-injection approach is also provided. In at least one approach, three injections are provided, with two injections at the distal end of a segment, simultaneous withdrawal of one of the injection sources, and one injection at the proximal end of the segment.

In an exemplary study, the first two injections at the distal end may deliver, for example, a volume of 1.5% NaCl and a volume of 0.5% NaCl, noting that any number of solutions, volumes, and concentrations thereof suitable for such a study could be utilized. In this exemplary study, the first two injections (1.5% NaCl and 0.5% NaCl) may be made at the distal point of the segment, wherein the catheter system is simultaneously withdrawn with the injection of the 0.5% NaCl so that the 0.5% NaCl may also be used for the proximal end. These injections would then be followed by a 1.5% NaCl injection at the proximal end of the segment.

Advantages to this particular approach over the four-injection approach are that (1) the conductivity would be simplified as that of 0.5% rather than blood, and (2) there are only three injections required instead of four. However, the three-injection method also requires that a physician using a catheter system to perform such a procedure would be required to inject and pull back simultaneously. A physician comfortable with simultaneous injection and pull back may prefer the three-injection approach, while a physician not comfortable with simultaneous injection and pull back may prefer the four-injection approach. Either approach is possible using the algorithm provided herein.

Ex-Vivo and In-Vivo Validation of Algorithm

Studies were performed ex-vivo in in-vivo to validate the algorithm provided herein. The former was validated in a carotid artery with an artificial stenosis to compare the algorithm disclosed herein versus cast measurements for both for the two-injection method at several discrete points and the reconstructed profile. The latter validation was done in vivo in a coronary artery (LAD) where a comparison between LR (LumenRecon) and IVUS (intravascular) was made.

Ex-Vivo Validation of Algorithm

Figure 9:
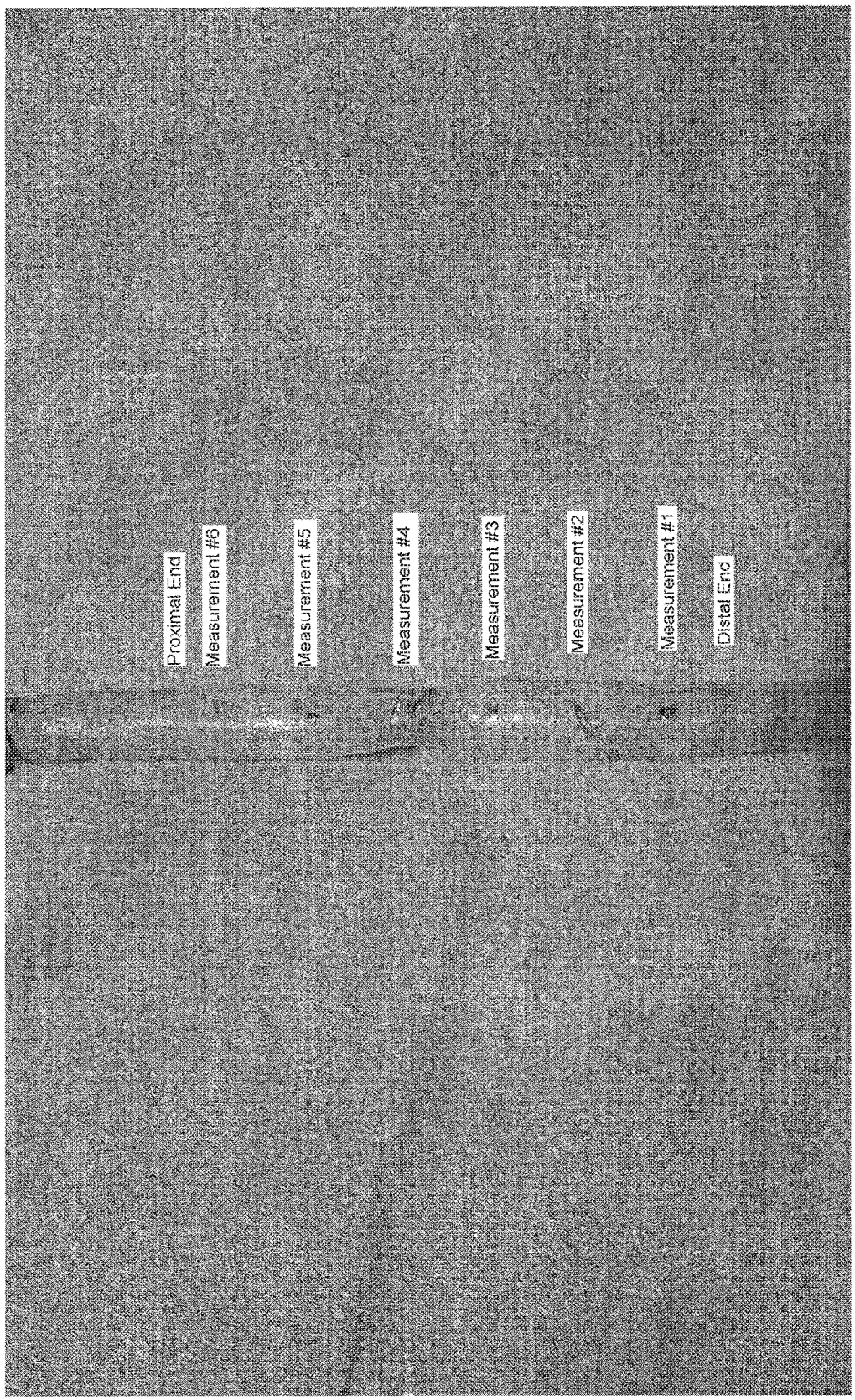
FIG. 9 shows a photograph of a segment of swine carotid artery used for performing ex-vivo validation of the algorithm of the present disclosure.

To validate the algorithm ex-vivo, a segment of a swine carotid artery was removed and mounted on a bench stand as shown in FIG. 9. A small portion of one end of the vessel was removed and used to create a stenosis around the vessel, which was accomplished by wrapping this piece of tissue around the middle of the vessel and shortening the piece of tissue using suture. A black indicator was used to mark the outside of the vessel at six locations along the length (length=3.23 cm). As shown in FIG. 9, the bottom portion of the vessel is the distal end, and black marks signify where LumenRecon measurements were made using a two-injection method of the present disclosure.

The LumenRecon system was calibrated using the 0.45% and 1.5% saline concentrations. A two-injection method according to the present disclosure was used to make single diameter measurements at the six locations along the length of the vessel. "Pull back" measurements were also made along the length of the vessel to create a continuous profile of the vessel diameter.

After the LumenRecon measurements were taken, a cast mold of the vessel was created. The diameter of the cast mold of the vessel was determined using microscopy. The cast measurements were taken at the six locations marked by the black indicator and at intermediate locations along the vessel.

Figure 10:
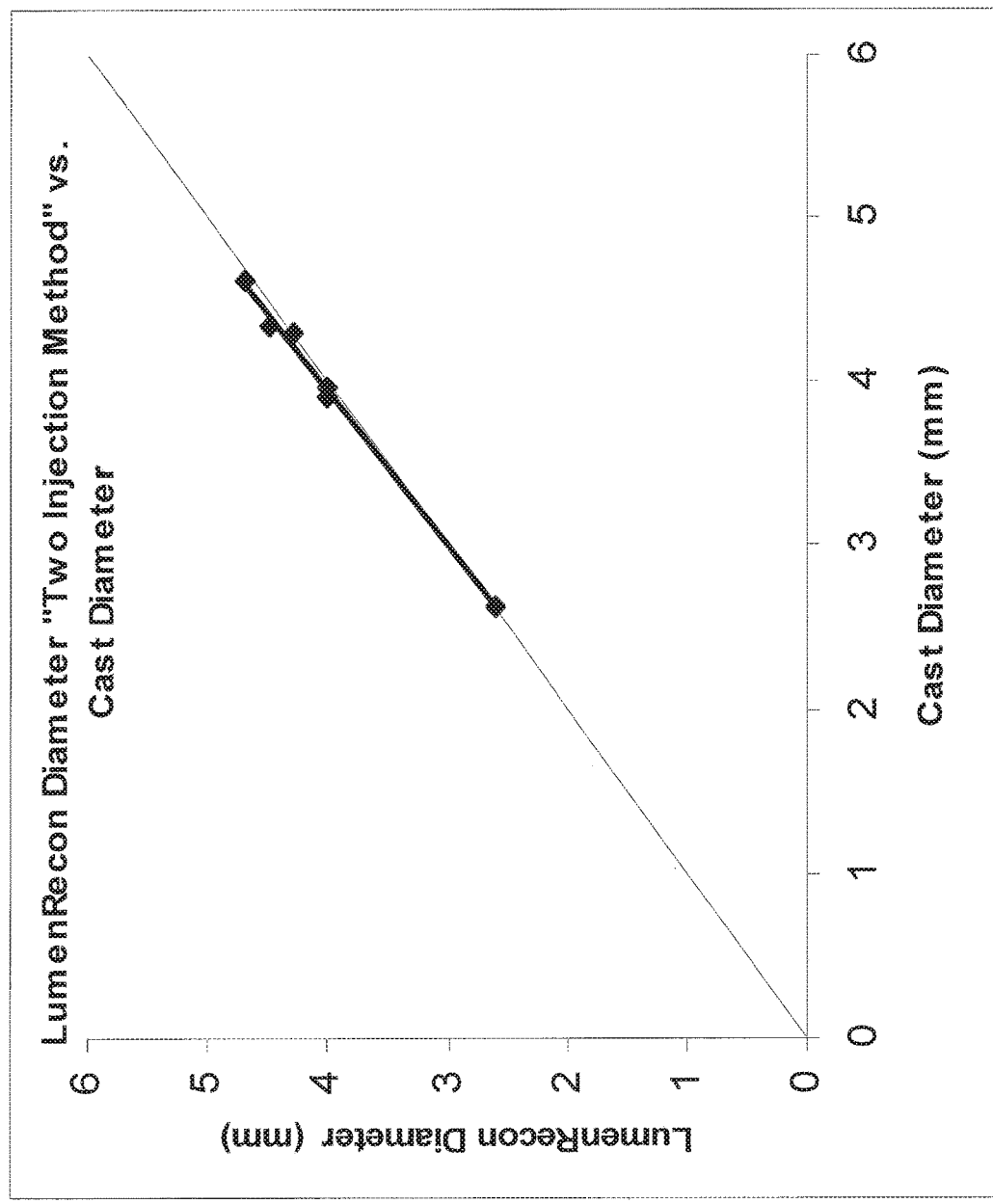
FIG. 10 shows ex-vivo data using a two-injection method of the present disclosure.
Figure 11:
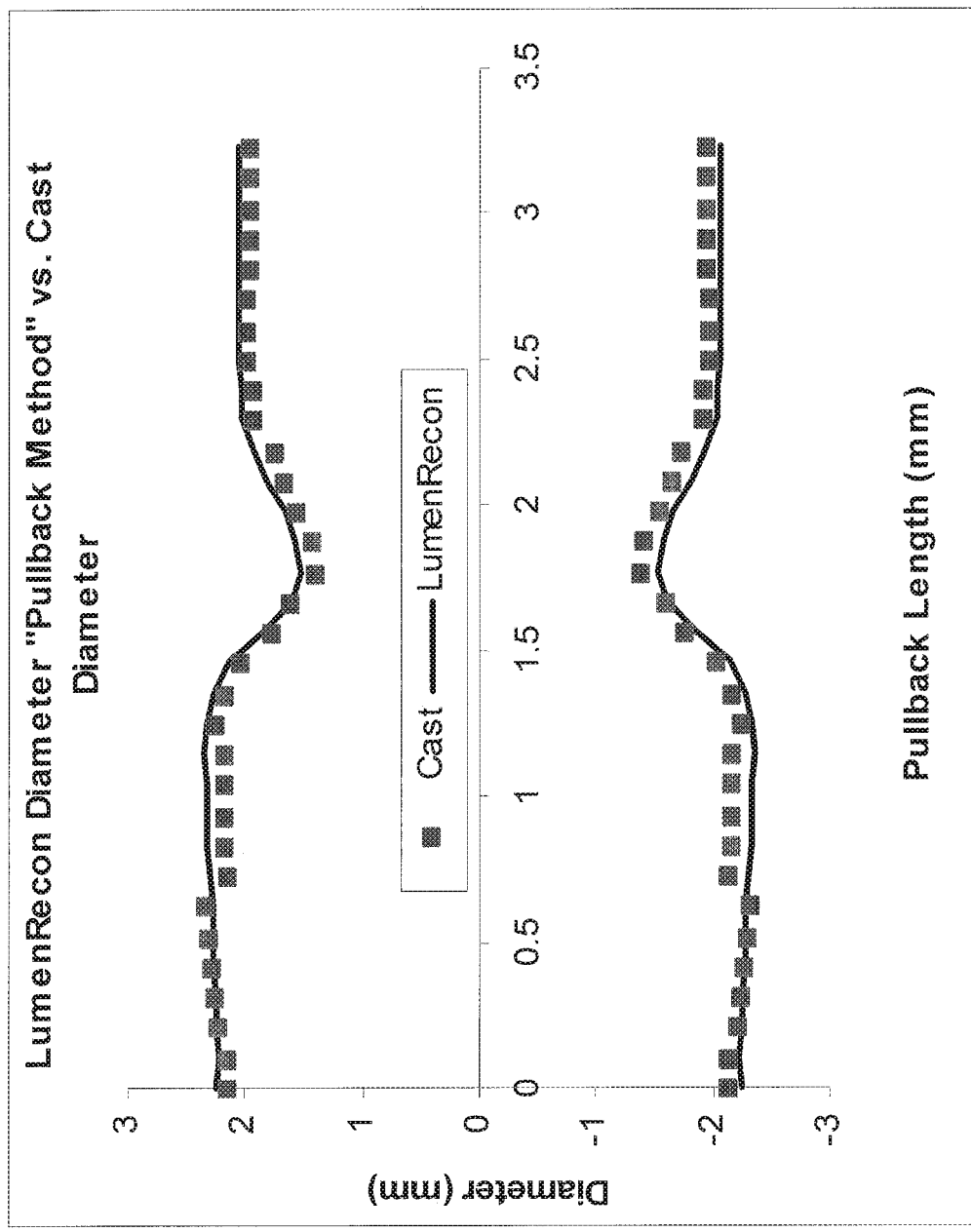
FIG. 11 shows ex-vivo data using a pull back method of the present disclosure.

The diameters from the LumenRecon two injection method and the pull back measurements were plotted against the cast measurements, respectively. FIG. 10 shows the data for the six locations using a two-injection method of the present disclosure, comparing the diameters calculated by the LumenRecon system to those measured from the cast mold of the vessel using microscopy. The least square fit of the data shows y=1.0599x−0.1805, $R^2$=0.9944. FIG. 11 shows a profile of data points (diameters) using a pull back method of the present disclosure, comparing the diameters calculated by the LumenRecon system to those measured from the cast mold of the vessel using microscopy.

In Vivo Validation

Figure 12:
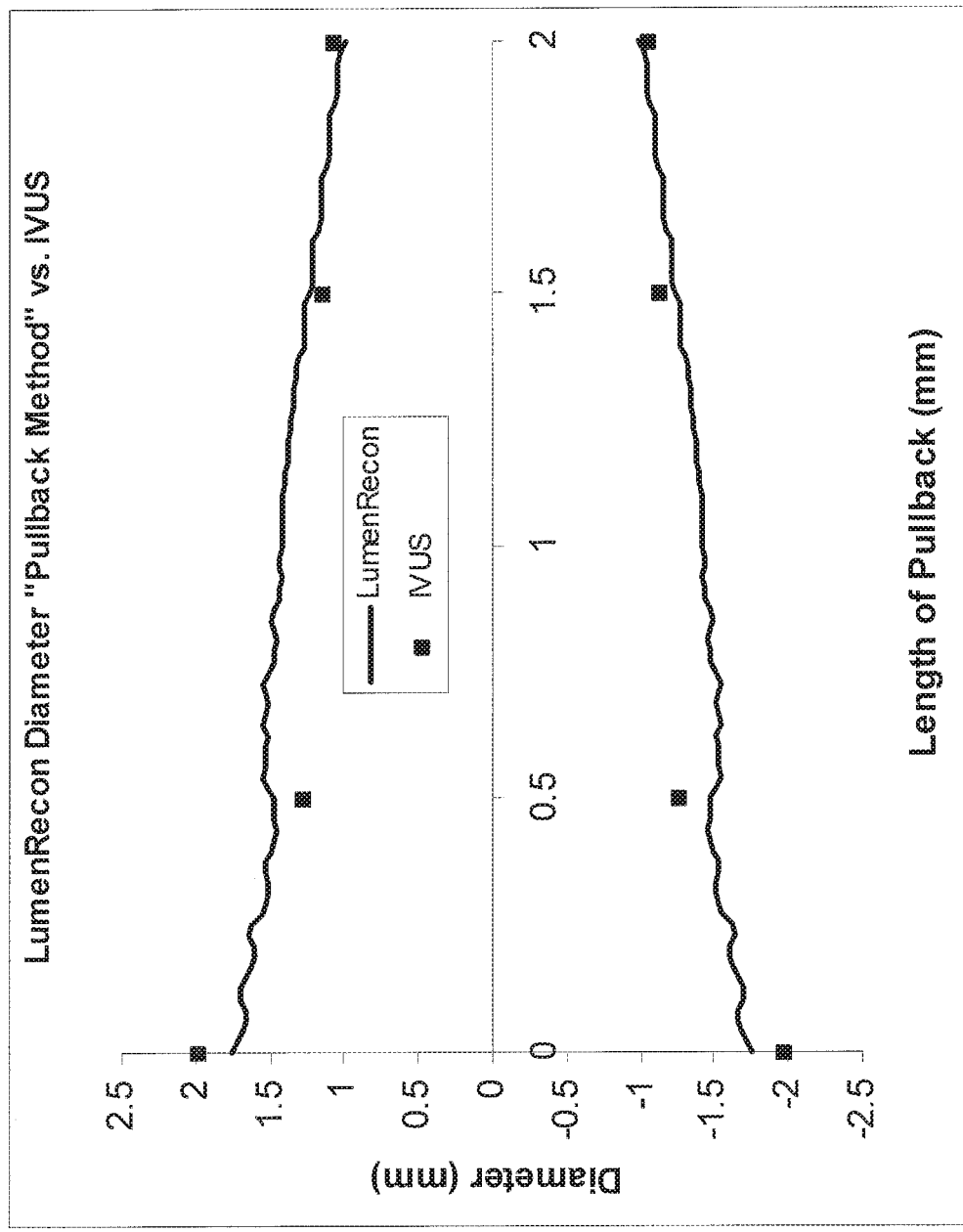
FIG. 12 shows in-vivo data using a two-injection method of the present disclosure as compared to the IVUS method.

The LumenRecon system was used to make measurements in the left anterior descending (LAD) coronary artery in an anesthesized swine. A two-injection method of the present disclosure was used to construct a profile which was compared to IVUS at four different locations along the profile. FIG. 12 shows the LumenRecon measurements plotted against the IVUS measurements, showing the measurements before and after the temperature correction. The temperature correction was incorporated into the calibration of the catheter. It was determined that a NaCl solution injected at room temperature (25° C.) reaches 30° C. when at the body site of measurement (39° C.). Hence, calibrations of fluid were made at 30° C. to account for the heating of the fluid during injection.

Figure 6:
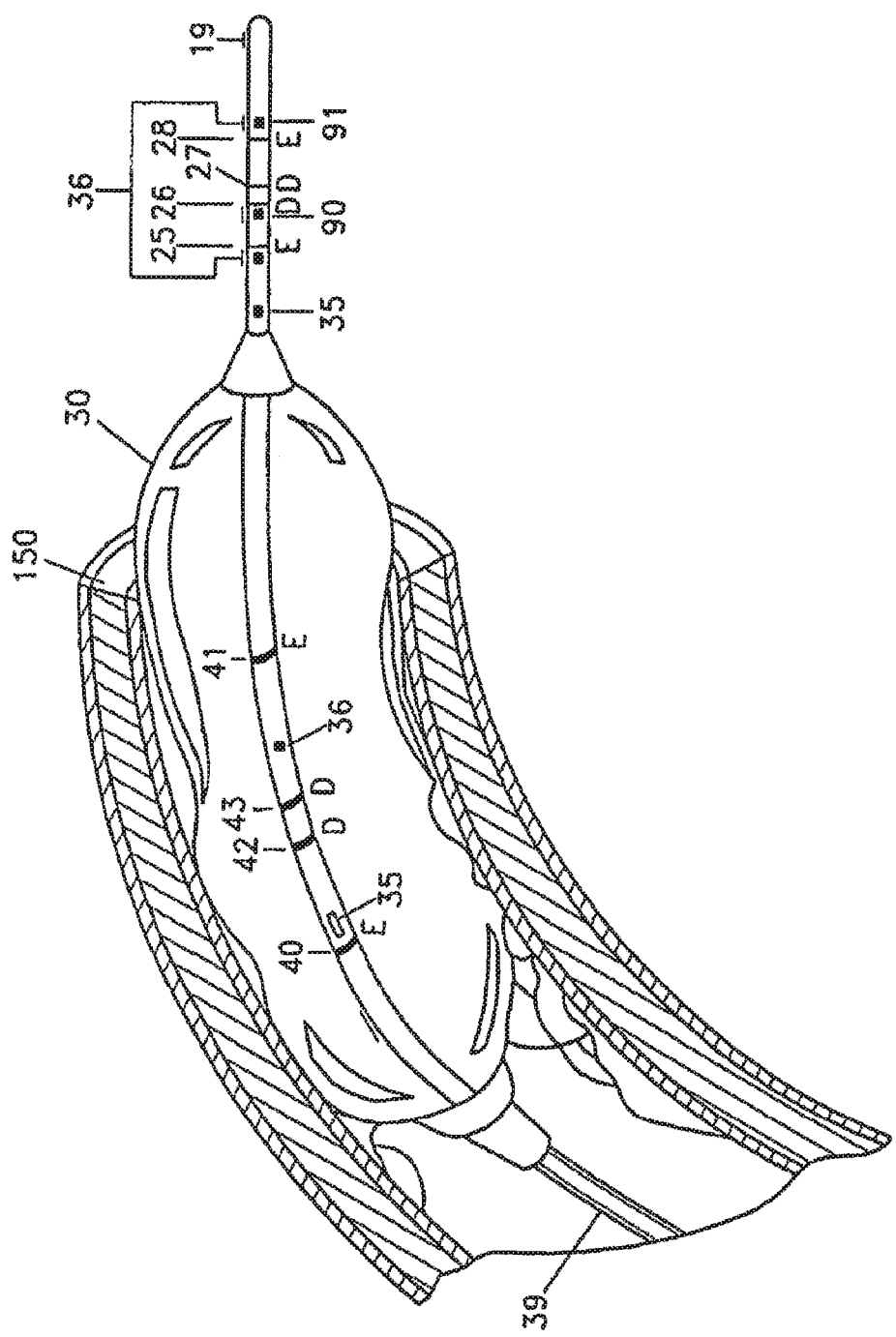
FIG. 6 illustrates balloon distension of the lumen of the coronary artery.
Figure 7:
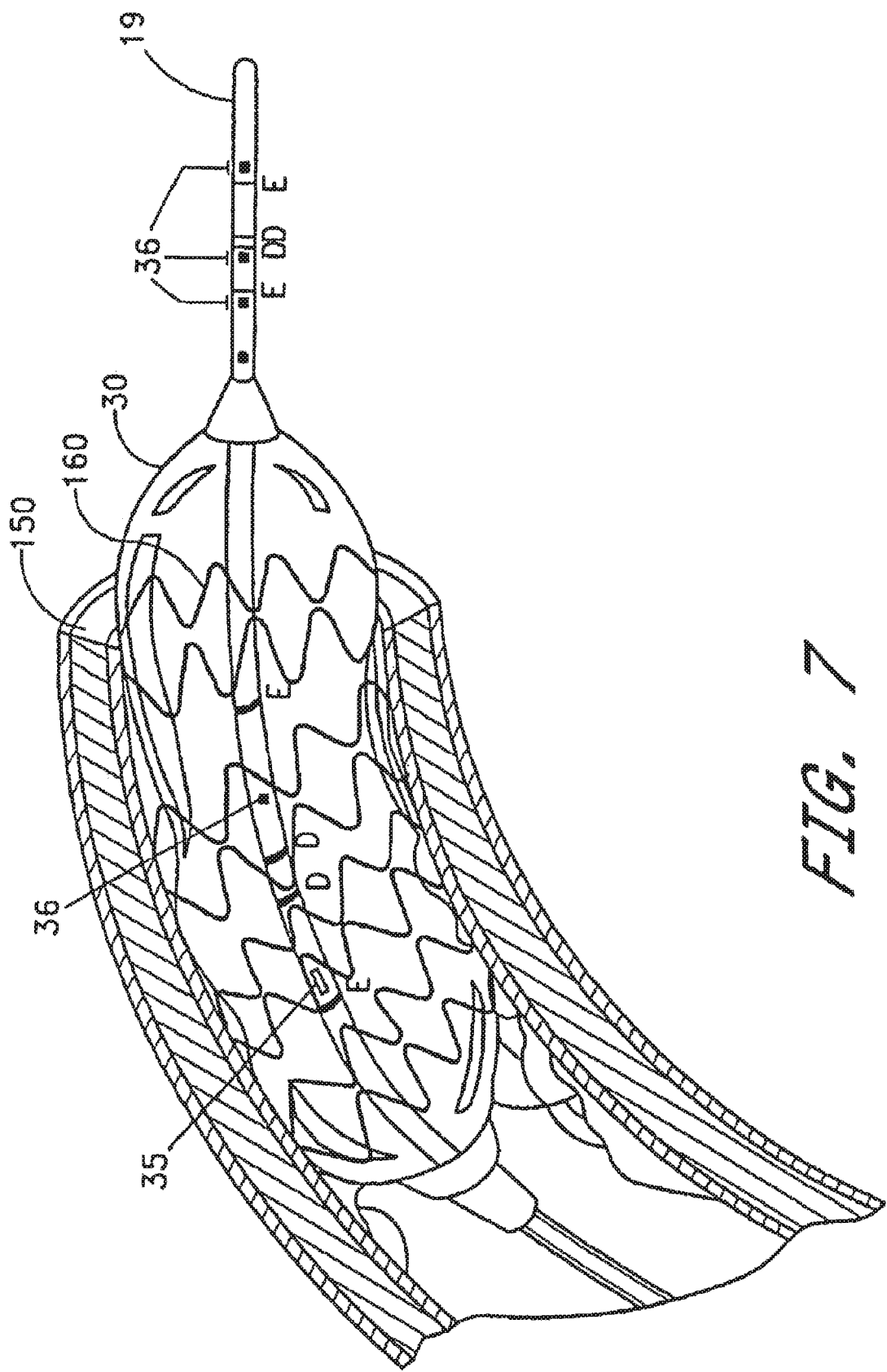
FIG. 7 illustrates balloon distension of a stent into the lumen of the coronary artery.

Referring to the embodiment shown in FIG. 6, the angioplasty balloon 30 is shown distended within the coronary artery 150 for the treatment of stenosis. As described above with reference to FIG. 1B, a set of excitation electrodes 40, 41 and detection electrodes 42, 43 are located within the angioplasty balloon 30. In another embodiment, shown in FIG. 7, the angioplasty balloon 30 is used to distend the stent 160 within blood vessel 150.

For valve area determination, it is not generally feasible to displace the entire volume of the heart. Hence, the conductivity of blood is changed by injection of hypertonic NaCl solution into the pulmonary artery which will transiently change the conductivity of blood. If the measured total conductance is plotted versus blood conductivity on a graph, the extrapolated conductance at zero conductivity corresponds to the parallel conductance. In order to ensure that the two inner electrodes are positioned in the plane of the valve annulus (2-3 mm), in one preferred embodiment, the two pressure sensors 36 are advantageously placed immediately proximal and distal to the detection electrodes (1-2 mm above and below, respectively) or several sets of detection electrodes (see, e.g., FIGS. 1D and 1F). The pressure readings will then indicate the position of the detection electrode relative to the desired site of measurement (aortic valve: aortic-ventricular pressure; mitral valve: left ventricular-atrial pressure; tricuspid valve: right atrial-ventricular pressure; pulmonary valve: right ventricular-pulmonary pressure). The parallel conductance at the site of annulus is generally expected to be small since the annulus consists primarily of collagen which has low electrical conductivity. In another application, a pull back or push forward through the heart chamber will show different conductance due to the change in geometry and parallel conductance. This can be established for normal patients which can then be used to diagnose valvular stensosis.

In one approach, for the esophagus or the urethra, the procedures can conveniently be done by swallowing fluids of known conductances into the esophagus and infusion of fluids of known conductances into the urinary bladder followed by voiding the volume. In another approach, fluids can be swallowed or urine voided followed by measurement of the fluid conductances from samples of the fluid. The latter method can be applied to the ureter where a catheter can be advanced up into the ureter and fluids can either be injected from a proximal port on the probe (will also be applicable in the intestines) or urine production can be increased and samples taken distal in the ureter during passage of the bolus or from the urinary bladder.

In one approach, concomitant with measuring the cross-sectional area and or pressure gradient at the treatment or measurement site, a mechanical stimulus is introduced by way of inflating the balloon or by releasing a stent from the catheter, thereby facilitating flow through the stenosed part of the organ. In another approach, concomitant with measuring the cross-sectional area and or pressure gradient at the treatment site, one or more pharmaceutical substances for diagnosis or treatment of stenosis is injected into the treatment site. For example, in one approach, the injected substance can be smooth muscle agonist or antagonist. In yet another approach, concomitant with measuring the cross-sectional area and or pressure gradient at the treatment site, an inflating fluid is released into the treatment site for release of any stenosis or materials causing stenosis in the organ or treatment site.

Again, it will be noted that the methods, systems, and devices described herein can be applied to any body lumen or treatment site. For example, the methods, systems, and devices described herein can be applied to any one of the following exemplary bodily hollow systems: the cardiovascular system including the heart; the digestive system; the respiratory system; the reproductive system; and the urogential tract.

Finite Element Analysis:

In one preferred approach, finite element analysis (FEA) is used to verify the validity of Equations [4] and [5]. There are two major considerations for the model definition: geometry and electrical properties. The general equation governing the electric scalar potential distribution, V, is given by Poisson's equation as:

$$\nabla \cdot (C \nabla V) = -I \quad [13]$$

where C, I, and $\nabla$ are the conductivity, the driving current density, and the del operator, respectively. Femlab or any standard finite element packages can be used to compute the nodal voltages using equation [13]. Once V has been determined, the electric field can be obtained from as $E = -\nabla V$.

The FEA allows the determination of the nature of the field and its alteration in response to different electrode distances, distances between driving electrodes, wall thicknesses and wall conductivities. The percentage of total current in the lumen of the vessel, % I, can be used as an index of both leakage and field homogeneity. Hence, the various geometric and electrical material properties can be varied to obtain the optimum design; i.e., minimize the non-homogeneity of the field. Furthermore, the experimental procedure was simulated by injection of the two solutions of NaCl to verify the accuracy of Equation [4]. Finally, an assessment of the effect of presence of electrodes and catheter in the lumen of vessel may be performed. The error terms representing the changes in measured conductance due to the attraction of the field to the electrodes and the repulsion of the field from the resistive catheter body were quantified.

Poisson's equation for the potential field was solved, taking into account the magnitude of the applied current, the location of the current driving and detection electrodes, and the conductivities and geometrical shapes in the model including the vessel wall and surrounding tissue. This analysis suggest that the following conditions are optimal for the cylindrical model: (1) the placement of detection electrodes equidistant from the excitation electrodes; (2) the distance between the current driving electrodes should be much greater than the distance between the voltage sensing electrodes; and (3) the distance between the detection and excitation electrodes is comparable to the vessel diameter or the diameter of the vessel is small relative to the distance between the driving electrodes. If these conditions are satisfied, the equipotential contours more closely resemble straight lines perpendicular to the axis of the catheter and the voltage drop measured at the wall will be nearly identical to that at the center. Since the curvature of the equipotential contours is inversely related to the homogeneity of the electric field, it is possible to optimize the design to minimize the curvature of the field lines. Consequently, in one preferred approach, one or more of conditions (1)-(3) described above are met to increase the accuracy of the cylindrical model.

Theoretically, it is impossible to ensure a completely homogeneous field given the current leakage through the vessel wall into the surrounding tissue. Research leading to the disclosure of the present application identified that the isopotential line is not constant as one moves out radially along the vessel as stipulated by the cylindrical model. In one embodiment, a catheter with a radius of 0.55 mm is considered whose detected voltage is shown in FIGS. 8A and 8B for two different NaCl solutions (0.5% and 1.5%, respectively). The origin corresponds to the center of the catheter. The first vertical line 220 represents the inner part of the electrode which is wrapped around the catheter and the second vertical line 221 is the outer part of the electrode in contact with the solution (diameter of electrode is approximately 0.25 mm). The six different curves, top to bottom, correspond to six different vessels with radii of 3.1, 2.7, 2.3, 1.9, 1.5, and 0.55 mm, respectively. It can be seen that a "hill" occurs at the detection electrode 220, 221 followed by a fairly uniform plateau in the vessel lumen followed by an exponential decay into the surrounding tissue. Since the potential difference is measured at the detection electrode 220, 221, the simulation generates the "hill" whose value corresponds to the equivalent potential in the vessel as used in Eq. [4]. Hence, for each catheter size, the dimension of the vessel was varied such that equation [4] is exactly satisfied. Consequently, the optimum catheter size for a given vessel diameter was obtained such that the distributive model satisfies the lumped equations (Equation [4] and [5]). In this way, a relationship between vessel diameter and catheter diameter may be generated such that the error in the CSA measurement is less than 5%.

In an exemplary embodiment, different diameter catheters are prepackaged and labeled for optimal use in certain size vessel. For example, for vessel dimension in the range of 4-5 mm, 5-7 mm or 7-10 mm, analysis in accordance with the disclosure of the present application shows that the optimum diameter catheters will be in the range of 0.9-1.4, 1.4-2.0 or 2.0-4.6 mm, respectively. A clinician can select the appropriate diameter catheter based on the estimated vessel diameter of interest. This decision will be made prior to the procedure and will serve to minimize the error in the determination of lumen CSA.

The present disclosure also includes disclosure of impedance devices having one or more electrodes or poles thereon. For device 101 (such as, for example, catheter 20, catheter 20A, catheter 20B, catheter 21, catheter 22, catheter 23, catheter 29, wire 18, and/or other impedance device embodiments referenced herein that are configured for use with one, two, three, or potentially more electrodes as described herein), embodiments having only one electrode/pole 102 thereon, therein, or otherwise coupled thereto (hereinafter referred to a "unipolar" devices 101), said devices 101 are operable to work with at least one external electrode/pole 145 to generate an electric field that can be detected by a detection electrode (another exemplary electrode/pole 102). Device 101 embodiments having more than one electrode/pole 102, such as an embodiment having two electrodes/poles 102, three electrodes/poles 102, or four or more electrodes/poles 102, may also be configured and operable to work with at least one external electrode/pole 102. For purposes of the present disclosure, the term "electrode/pole" refers to an electrode or another item operable as a pole, such as a metallic clip, button, pad, sheath, lead, wire, or other item, wherein the item can work with another electrode/pole to generate an electric field. Electrodes/poles 102 of the present disclosure may also include one or more of electrodes 25, 26, 27, 28, 40, 41, 42, 43, 51, 52, 53, 54, 55, 56, and/or 57, as generally referenced herein if configured for use in connection with a particular embodiment.

Figure 13A:
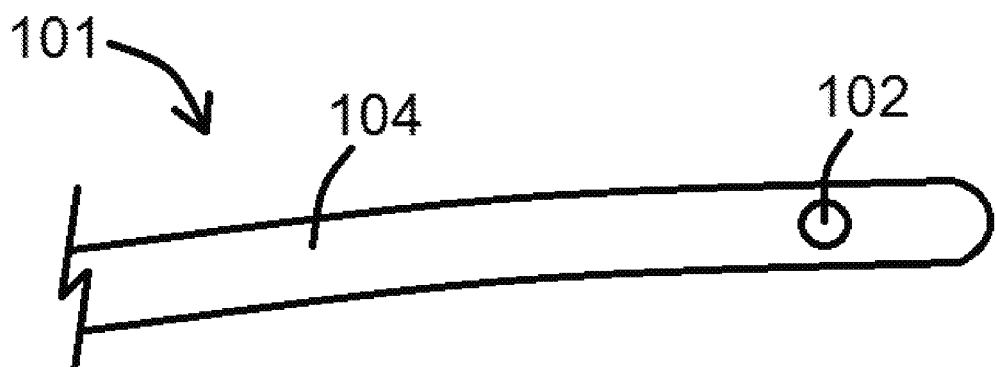
FIG. 13A shows a distal portion of a unipolar device, according to an exemplary embodiment of the present disclosure.

FIG. 13A shows a distal portion of an exemplary device 101 of the present disclosure having one electrode/pole 102 thereon, therein, or otherwise coupled thereto. Such a device 101 is referred to herein as a "unipolar device," as it has one electrode/pole 102 thereon, therein, or otherwise coupled thereto. Such a device 101, in various embodiments, is used to perform a unipolar method of detection within a mammalian body.

With a unipolar device 101 configuration, and in general, said device 101 has a single electrode/pole 102 that has both excitation and detection functionality. "Excitation," as referenced herein, refers to the ability to generate an electric field that a detection electrode/pole 102 can detect at least one conductance measurement within in connection with one or more methods of the present disclosure. Phrased differently, an electrode/pole 102, in a unipolar device 101 embodiment, needs to be able to can excite a field and detect within said field.

Generation of an electric field using a unipolar device 101 embodiment requires a second electrode/pole 102 positioned somewhere other than device 101. For example, a second electrode/pole 102 may comprise part of a patch 130, part of a sheath 140, a clip 145, and/or another item that, when used with the electrode/pole 102 of unipolar device 101, can allow for a field to be excited and conductance measurements to be obtained within said field. Should there only be two total electrodes/poles 102 (one on device 101 and one not on device 101), both electrodes/poles 102 would operate to excite/generate a field and detect within a field. If a unipolar device 101 is used in connection with two additional items (electrodes/poles 102 and/or items including electrodes/poles 102), then the electrode/pole 102 on device 101 would still have excitation and detection functionality, but the other two electrodes/poles 102 would not require dual functionality, as long as one electrode/pole 102 can work with the electrode/pole 102 on device 101 to excite a field, and as long as another electrode/pole 102 can work with the electrode/pole 102 on device to detect within the excited field.

Figure 14:
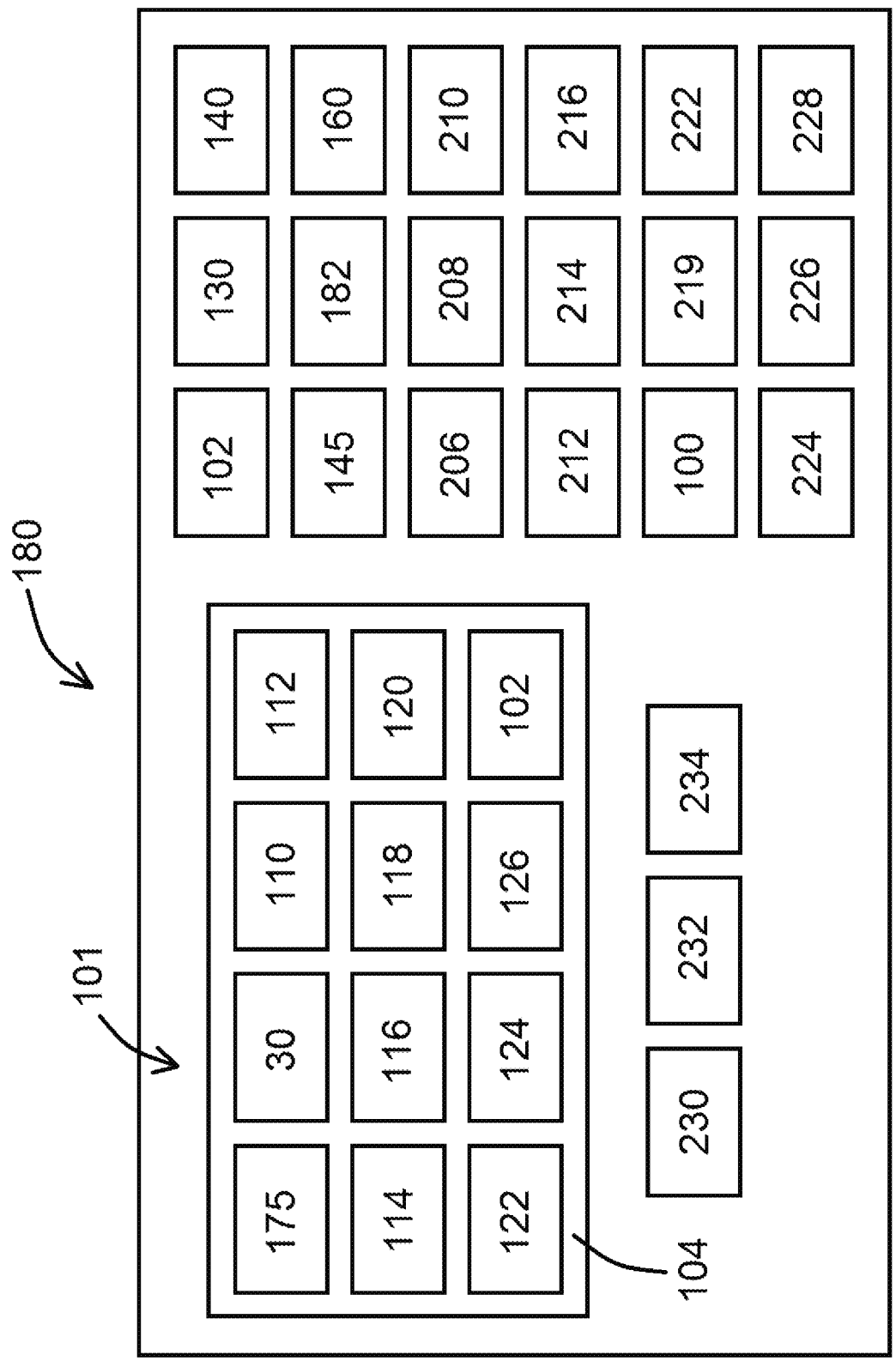
FIG. 14 shows a block diagram of device and system components and features, according to an exemplary embodiment of the present disclosure.

Devices 101 of the present disclosure can comprise a number of components/features. For example, devices 101 may be wires or catheters, and thus having an elongated body 104 (such as present with the various impedance devices referenced herein) with one or more lumens 175 optionally defined therethrough (such as in catheter device 101 embodiments). Lumens 175, as referenced herein, may include lumens 60, 71, pressure conduit 95A, pressure conduit 95B, and/or tunnel 96, as generally referenced herein. Additional components, such as one or more balloons 30, pressure sensors 110 (which may be a sensor or may be configured as a pressure port 36, 90, and/or 91 as generally referenced herein), temperature sensors 112, ablation contacts 114, cutting portions 116, and/or other components/features known in the intravascular device art thereon, therein, or otherwise coupled thereto. Furthermore, devices 101 may define one or more apertures 118, grooves 120, housings 122 (such as to house a balloon 30), suction ports 124 (which may be, for example, an infusion port 35, 36, and/or 37, in various embodiments), and/or vacuum ports 126 therein. FIG. 14 shows a block component diagram of an exemplary device 101 of the present disclosure, wherein device 101 comprises the various components referenced herein. Other device 101 embodiments may have more or less components than as shown therein. For example, an exemplary unipolar device 101 embodiment may comprise an elongated body 104 configured as a wire, one electrode/pole 102, a temperature sensor 112, and an ablation contact 114.

A combination of an exemplary device 101 of the present disclosure plus one other component external to the device, such as another electrode/pole 102, a patch 130, a sheath 140, a clip 145, or another item, would comprise an exemplary system 180 of the present disclosure. The component diagram shown in FIG. 14 also shows that an exemplary system 180 of the present disclosure can comprise an exemplary device 101 of the present disclosure and one or more other components, such as one or more electrodes/poles 102, patches 130, sheaths 140, clips 145, and/or other items. Further, an exemplary system 180 of the present disclosure may comprise the use of one or more additional components, such as a second catheter 182 (such as, for example, a guide catheter 23 as generally referenced herein), a stent 160, a valve device 206, a lead 208, a second wire 210, a needle 212, a diagnostic device 214, and/or a therapeutic device 216, for example. In addition, an exemplary system 180 of the present disclosure may comprise a data acquisition and processing system 100, a processor 219 (which may be or comprise part of a computer 160 and/or a data acquisition and processing system 100, in various embodiments), a storage medium 222, a power source 224, an injection source 226 (such as, for example, a system 105 or 106 as generally referenced herein), and/or a vacuum source 228 (such as, for example, a system 106 referenced herein). Various components of devices 101 and/or systems 180 of the present disclosure may be coupled to one another, or otherwise in communication with one another, so to operate as intended, such as through one or more wires 230 (such as, for example, electrical leads 70A or 70B or other types of wires/leads), tubes 232, and/or connectors 234.

Figure 13B:
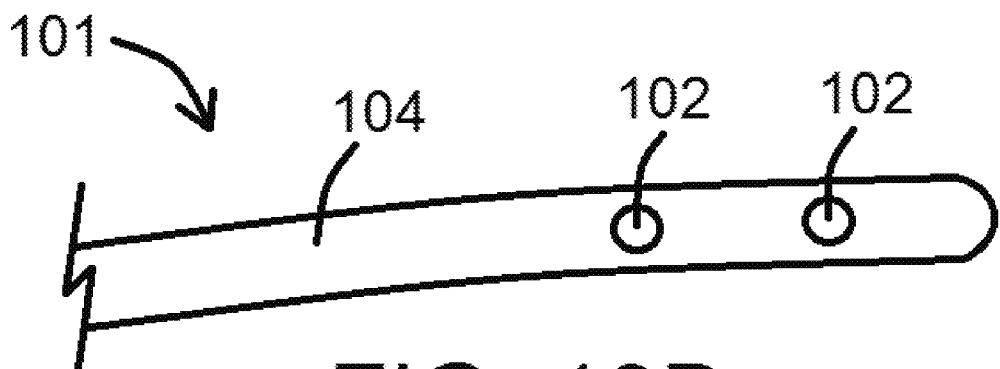
FIG. 13B shows a distal portion of a bipolar device, according to an exemplary embodiment of the present disclosure.

FIG. 13B shows a distal portion of an exemplary device 101 of the present disclosure having two electrodes/poles 102 thereon, therein, or otherwise coupled thereto. Such a device 101 is referred to herein as a "bipolar device," as it has two electrodes/poles 102 thereon, therein, or otherwise coupled thereto. Such a device 101, in various embodiments, is used to perform a bipolar method of detection within a mammalian body.

Generation of an electric field using a bipolar device 100 can be performed using the two electrodes/poles 102 thereon, therein, or otherwise coupled thereto, by way of an excitation functionality of said electrodes/poles 102. If both electrodes/poles 102 can excite an electric field and detect within the electric field, only two electrodes/poles 102 are required. However, if only one electrode/pole 102 can excite an electric field, such an embodiment requires an additional electrode/pole 102 positioned on device 100 or somewhere other than device 100. For example, an additional electrode/pole 102 may comprise part of a patch 130, part of a sheath 140, a clip 150, and/or another item that, when used with one of the electrodes/poles 102 of bipolar device 100, can allow for a field to be excited and conductance measurements to be obtained within said field. Should there only be three total electrodes/poles 102 (two on device 100 and one not on device 100), one electrode/pole on device 100 would operate to excite/generate a field and detect within a field, and the other electrode/pole on device 100 would operate to detect within the field. If a bipolar device 100 is used in connection with two additional items (electrodes/poles 102 and/or items including electrodes/poles 102), then one electrode/pole 102 on device 100 would be operable to excite a field and other would be operable to detect within the field, and one of the electrodes/poles 102 outside of the device 100 would be operable to excite a field, and the other electrode/pole outside of device 100 would be operable to detect within the field.

Figure 13C:
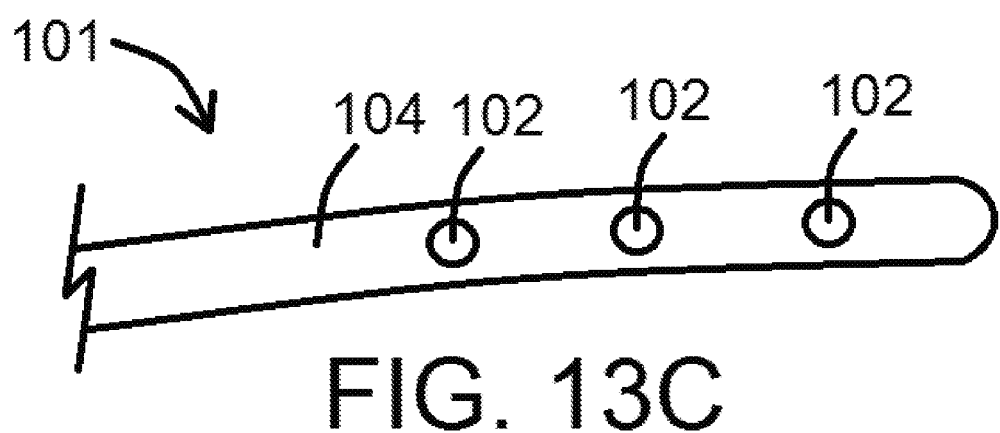
FIG. 13C shows a distal portion of a tripolar device, according to an exemplary embodiment of the present disclosure.

FIG. 13C shows a distal portion of an exemplary device 101 of the present disclosure having three electrodes/poles 102 thereon, therein, or otherwise coupled thereto. Such a device 101 is referred to herein as a "tripolar device," as it has three electrodes/poles 102 thereon, therein, or otherwise coupled thereto. Such a device 101, in various embodiments, is used to perform a tripolar method of detection within a mammalian body.

Generation of an electric field using a tripolar device 100 can be performed using two electrodes/poles 102 of device 100 by way of an excitation functionality of said electrodes/poles 102. If two electrodes/poles 102 of device can excite an electric field and two electrodes/poles 102 of device can excite and detect within the electric field (where one electrode/pole 102 can excite and detect within the field), only three electrodes/poles 102 are required. However, if only one electrode/pole 102 of device 100 can excite an electric field, such an embodiment requires an additional electrode/pole 102 positioned somewhere other than device 100. For example, an additional electrode/pole 102 may comprise part of a patch 130, part of a sheath 140, a clip 150, and/or another item that, when used with one of the electrodes/poles 102 of tripolar device 100, can allow for a field to be excited and conductance measurements to be obtained within said field. In such an embodiment, one electrode/pole 102 on device 100 would be used to excite the field, and the other two electrodes/poles 102 would be used to detect within the field, while the electrode/pole 102 outside of the device 100 would also be used to excite the field.

A tetrapolar device 101 would include four electrodes/poles 102 on device 101, wherein two electrodes/poles 102 (also referred to as excitation electrodes) would operate to generate a field, while the other two electrodes/poles 102 (also referred to as detection electrodes), would be positioned in between the two excitation electrodes and detect within a field. Such devices are as disclosed within U.S. Pat. No. 7,454,244 to Kassab et al., the entire contents of which are hereby incorporated into the present disclosure by reference. Such devices would be used to perform tetrapolar methods, which could involve, in some embodiments, the use of one or more fluid injections (saline, for example), in connection with the performance of the same, as described within said patent.

Conductance measurements obtained using devices 101 and/or systems 180 of the present disclosure may use various formulas and/or algorithms, such as Ohm's Law and/or a distance between two electrodes/poles 102 used to detect within an electric field, one or more saline injections, etc., as described in one or more of the following references, wherein said devices 101 and/or systems are configured to perform one or more of the following procedures/tasks:

(a) determining the size (cross-sectional area or diameter, for example) of a mammalian luminal organ, parallel tissue conductance within a mammalian luminal organ, and/or navigation of a device within a luminal organ, such as described within U.S. Pat. No. 7,454,244 to Kassab et al., U.S. Pat. No. 8,114,143 to Kassab et al., U.S. Pat. No. 8,082,032 to Kassab et al., U.S. Patent Application Publication No. 2010/0152607 of Kassab, U.S. Patent Application Publication No. 2012/0053441 of Kassab, U.S. Patent Application Publication No. 2012/0089046 of Kassab et al., U.S. Patent Application Publication No. 2012/0143078 of Kassab et al., and U.S. Patent Application Publication No. 2013/0030318 of Kassab, the entire contents of which are hereby incorporated into the present disclosure by reference;

(b) determining the location of one or more body lumen junctions and/or profiles of a luminal organ, such as described within U.S. Patent Application Publication No. 2009/0182287 of Kassab, U.S. Patent Application Publication No. 2012/0172746 of Kassab, U.S. Patent Application Publication No. 2010/0010355 of Kassab, and U.S. Pat. No. 8,078,274 to Kassab, the entire contents of which are hereby incorporated into the present disclosure by reference;

(c) ablating a tissue within a mammalian patient and/or removing stenotic lesions from a vessel, such as described within U.S. Patent Application Publication No. 2009/0182287 of Kassab, U.S. Patent Application Publication No. 2009/0204134 of Kassab, and U.S. Patent Application Publication No. 2010/0222786 of Kassab, the entire contents of which are hereby incorporated into the present disclosure by reference;

(d) determining the existence, potential type, and/or vulnerability of a plaque within a luminal organ, such as described within U.S. Patent Application Publication No. 2010/0152607 of Kassab, U.S. Patent Application Publication No. 2011/0034824 of Kassab, and U.S. Pat. No. 7,818,053 to Kassab, the entire contents of which are hereby incorporated into the present disclosure by reference;

(e) determining phasic cardiac cycle measurements and determining vessel compliance, such as described within U.S. Pat. No. 8,185,194 to Kassab and U.S. Pat. No. 8,099,161 to Kassab, the entire contents of which are hereby incorporated into the present disclosure by reference;

(f) determining the velocity of a fluid flowing through a mammalian luminal organ, such as described within U.S. Pat. No. 8,078,274 to Kassab, U.S. Patent Application Publication No. 2010/0152607 of Kassab, U.S. Patent Application Publication No. 2012/0053441 of Kassab et al., and U.S. Patent Application Publication No. 2012/0089046 of Kassab et al., the entire contents of which are hereby incorporated into the present disclosure by reference;

(g) sizing of valves using impedance and balloons, such as sizing a valve annulus for percutaneous valves, as described within U.S. Patent Application Publication No. 2010/0168836 of Kassab, the entire contents of which are hereby incorporated into the present disclosure by reference;

(h) detecting and/or removing contrast from mammalian luminal organs, such as described within U.S. Pat. No. 8,388,604 to Kassab, the entire contents of which are hereby incorporated into the present disclosure by reference;

(i) determining fractional flow reserve, such as described within U.S. Patent Application Publication No. 2011/0178417 of Kassab and U.S. Patent Application Publication No. 2011/0178383 of Kassab, the entire contents of which are hereby incorporated into the present disclosure by reference; and/or (j) to place leads within a mammalian luminal organ, such as by using a device 101 of the present disclosure to navigate through a mammalian luminal organ to a location of interest, and using device 101 and/or a second device to place a lead within said luminal organ.

In addition to the foregoing, various devices 101 of the present disclosure, and various other impedance devices as described in one or more of the aforementioned patents and/or patent applications (such as tetrapolar devices), may be operable to perform one or more of the following additional procedures/tasks:

(x) Ablate Relatively Small Veins.

Various devices 101 of the present disclosure, and various other impedance devices as described in one or more of the aforementioned patents and/or patent applications (such as tetrapolar devices), may be used to navigate through mammalian luminal organs for Endovascular Laser Therapy (EVLT) for treatment of venous insufficiency of varicose veins (cosmetic procedures). One objective is to ablate a smaller vein (such as saphenous vein and/or a popliteal vein) as opposed to a larger vein (such as a femoral vein or a common femoral vein. EVLT procedures are currently performed within a physician's office using ultrasound (US) and not fluoroscopy. In obese patients, the saphenous popliteal junction is difficult to image with US. As such, a laser catheter (an exemplary or other suitable ablation device (such as a device with an ablation contact/portion 114 thereon)) is delivered over an impedance wire (an exemplary device 101 of the present disclosure or a tetrapolar device as referenced herein), which may be, for example, a 0.035" guidewire. Use of such a device for navigation (peripherally), one can differentiate (based on a vessel profile) large from small veins, and also can size the luminal organ in connection with one or more saline injections, for example), prior to ablation, and/or (y) Navigation for Urological Uses.

Various devices 101 of the present disclosure, and various other impedance devices as described in one or more of the aforementioned patents and/or patent applications (such as tetrapolar devices), may be used to measure ureter stenosis at different levels, including at level of ureter emerging from the kidney, as well as to measure the urethra/urinary bladder junction, strictures of abnormal congenital ureter in children, enlargement of ureter in pregnant women due to compression of the uterus against ureter, trauma with pelvic fracture, and other urological conditions. Diagnosis of a urinary obstruction is currently largely established by x-ray studies, noting that the prostate and testis are most vulnerable to x-ray. These studies include kidney x-ray, kidney ultrasound, CAT scan, intravenous pyelogram (IVP) and MRI. Some of these studies may require administration of oral or intravenous contrast (dye) and even diuretics drugs which are painful to the patient and require x-ray exposure. To overcome these problems, said devices could be used to navigate through a ureter and obtain measurements therein to potentially identify a stenosis or other ureter size abnormality.

It can be appreciated that any number of devices may be used in accordance within the scope of the present disclosure, including, but not limited to, any number of catheters and/or wires. In exemplary embodiments, catheters, including, but not limited to, impedance and/or guide catheters, and wires, including, but not limited to, impedance wires, guide wires, pressure wires, and flow wires, may be used as appropriate as devices, systems, and/or portions of systems of the present disclosure, and may be used as appropriate to perform one or more methods, or steps thereof, of the present disclosure.

While various embodiments of impedance devices and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. An impedance device, comprising:
   an elongated body having a distal body end;
   only one electrode located along a longitudinal axis of the elongated body, the only one electrode configured to operate as both an excitation electrode and a detection electrode to obtain one or more conductance values within a mammalian luminal organ within an electric field; and
   wherein the impedance device is configured to communicate with a data acquisition and processing system that is configured to calculate a measured parameter of the mammalian luminal organ based upon the one or more conductance values obtained by the only one electrode.

2. The impedance device of claim 1, wherein the one electrode is configured to generate the electric field with an external electrode within a mammalian body when the external electrode is not coupled to the elongated body and is positioned upon or within the mammalian body and when the one electrode and the external electrode are activated.

3. The impedance device of claim 1, wherein the one electrode is configured to detect the electric field generated by the one electrode and the external electrode.

4. The impedance device of claim 1, wherein the elongated body is selected from the group consisting of an elongated wire and an elongated catheter.

5. The impedance device of claim 1, further comprising:
   a pressure sensor configured to detect a pressure within the mammalian luminal organ when at least part of the impedance device is positioned therein.

6. The impedance device of claim 1, further comprising:
   a temperature sensor configured to detect a temperature within the mammalian luminal organ when at least part of the impedance device is positioned therein.

7. The impedance device of claim 1, wherein the elongated body is configured as a catheter, and whereby the elongated body further defines a suction/infusion port in communication with a lumen of the elongated body configured so that a fluid can be injected through the lumen and out of the suction/infusion port.

8. An impedance system, comprising:
   an elongated body having only one electrode located along a longitudinal axis of the elongated body, wherein the one electrode is configured to obtain one or more conductance values within a mammalian luminal organ within an electric field and operate as both an excitation electrode and a detection electrode;
   a data acquisition and processing system in communication with the impedance system and configured to receive and process data from only the one electrode located along the longitudinal axis of the elongated body, to calculate a measured parameter of the mammalian luminal organ;
   wherein the measured parameter is calculated based upon the one or more conductance values obtained by only the one electrode located along the longitudinal axis of the elongated body;
   a first external electrode that is not coupled to the elongated body.

9. The impedance system of claim 8, wherein the first external electrode is configured to operate as an excitation electrode and a detection electrode.

10. The impedance system of claim 8, wherein the first external electrode comprises part of device selected from the group consisting of a patch, a sheath, and a clip.

11. The impedance system of claim 8, wherein the elongated body is selected from the group consisting of an elongated wire and an elongated catheter.

12. The impedance system of claim 8, further comprising:
    wherein the measured parameter is selected from the group consisting of a luminal organ diameter and a luminal organ cross-sectional area.

13. The impedance system of claim 8, further comprising:
    a pressure sensor configured to detect a pressure within the mammalian luminal organ when at least part of the elongated body is positioned therein.

14. The impedance system of claim 8, further comprising:
    a temperature sensor configured to detect a temperature within the mammalian luminal organ when at least part of the elongated body is positioned therein.

15. A method of using an impedance device, the method comprising the steps of:
    introducing at least part of an impedance device into a mammalian luminal organ at a first location, the impedance device comprising:

an elongated body having a longitudinal axis, only one electrode located along the longitudinal axis of the elongated body, wherein the one electrode obtains one or more conductance values within a mammalian luminal organ within an electric field, and wherein the one electrode operates as both an excitation electrode and a detection electrode; and providing electrical current to the only electrode and a first external electrode not coupled to the elongated body to generate the electric field, the first external electrode positioned upon or within a mammalian body having the mammalian luminal organ;

obtaining at least one conductance value using only the one electrode located along the longitudinal axis of the elongated body within the electric field;

calculating a measured parameter of the mammalian luminal organ based upon the at least one conductance value.

16. The method of claim 15, wherein the measured parameter is selected from the group consisting of a luminal organ diameter and a luminal organ cross-sectional area.

\* \* \* \* \*